(12) United States Patent
Sigoillot et al.

(10) Patent No.: US 9,688,966 B2
(45) Date of Patent: Jun. 27, 2017

(54) **COMPOSITIONS COMPRISING CELLOBIOSE DEHYDROGENASE FROM *PYCNOPORUS CINNABARINUS* AND THEIR USE FOR THE DEGRADATION OF LIGNOCELLULOSIC BIOMASS**

(75) Inventors: Jean-Claude Sigoillot, Six Fours les Plages (FR); Jean-Guy Berrin, Marseilles (FR); Mathieu Bey, Toulon (FR)

(73) Assignees: INSTITUT NATIONAL DE LA RECHERCHE AGRONOMIQUE, Paris (FR); INSTITUT FRANCAIS DU PETROLE ENERGIE NOUVELLE, Rueil Malmaison (FR); AGRO INDUSTRIES RECHERCHES ET DEVELOPPEMENTS, Pomacle (FR)

( * ) Notice: Subject to any disclaimer, the term of this patent is extended or adjusted under 35 U.S.C. 154(b) by 107 days.

(21) Appl. No.: 14/130,961

(22) PCT Filed: Jul. 4, 2012

(86) PCT No.: PCT/EP2012/002808
§ 371 (c)(1),
(2), (4) Date: Apr. 8, 2014

(87) PCT Pub. No.: WO2013/004377
PCT Pub. Date: Jan. 10, 2013

(65) Prior Publication Data
US 2014/0212927 A1 Jul. 31, 2014

Related U.S. Application Data

(60) Provisional application No. 61/504,426, filed on Jul. 5, 2011.

(51) Int. Cl.
| | | |
|---|---|---|
| *C12N 9/24* | (2006.01) | |
| *C12N 9/04* | (2006.01) | |
| *C12P 7/10* | (2006.01) | |
| *C12P 7/58* | (2006.01) | |
| *C12P 19/02* | (2006.01) | |
| *C12P 19/12* | (2006.01) | |
| *C12P 19/14* | (2006.01) | |
| *C13K 1/02* | (2006.01) | |
| *D21C 5/00* | (2006.01) | |
| *C12N 9/42* | (2006.01) | |

(52) U.S. Cl.
CPC ......... *C12N 9/0006* (2013.01); *C12N 9/2437* (2013.01); *C12N 9/2445* (2013.01); *C12P 7/10* (2013.01); *C12P 7/58* (2013.01); *C12P 19/02* (2013.01); *C12P 19/12* (2013.01); *C12P 19/14* (2013.01); *C13K 1/02* (2013.01); *D21C 5/005* (2013.01); *C12P 2203/00* (2013.01); *Y02E 50/16* (2013.01)

(58) Field of Classification Search
CPC .............................. C12P 2201/00; C12N 9/24
USPC .......................................................... 530/350
See application file for complete search history.

(56) References Cited

U.S. PATENT DOCUMENTS 8,809,033 B2 * 8/2014 Sweeney ................. C12P 19/02
435/207
2010/0159536 A1 * 6/2010 Sweeney ................. C12P 19/02
435/101

OTHER PUBLICATIONS

Moukha et al. Gene, 234, 23-33, 1999.*

* cited by examiner

*Primary Examiner* — Maryam Monshipouri
(74) *Attorney, Agent, or Firm* — Young & Thompson

(57) ABSTRACT

Enzyme compositions including at least a) a cocktail of cellulases from *Trichoderma reesei*, and b) an enzymatic cocktail from *Pycnoporus cinnabarinus* including a cellobiose dehydrogenase (CDH) or c) a recombinant cellobiose dehydrogenase (CDH) from *Pycnoporus cinnabarinus*, preferably also including a Family 61 glycoside hydrolase. Also, methods for degrading a lignocellulosic biomass, for producing a fermentation product, for producing gluconic acid, xylonic acid and/or xylobionic acid, for enhancing the production of gluconic acid, xylonic acid and/or xylobionic acid or for increasing the yield of sugars from a lignocellulosic biomass.

28 Claims, 15 Drawing Sheets

A

B

A

B

C

A

B

C

D

A

SEQUENCE LISTING

```
<160> NUMBER OF SEQ ID NOS: 14

<210> SEQ ID NO 1
<211> LENGTH: 769
<212> TYPE: PRT
<213> ORGANISM: Pycnoporus cinnabarinus

<400> SEQUENCE: 1

Met Lys Leu Gln His Leu Leu Leu Ser Leu Leu Pro Leu Ala Ser Ser
1               5                   10                  15

Val Tyr Ala Gln Val Ala Ala Pro Tyr Val Asp Ser Gly Asn Gly Phe
            20                  25                  30

Val Phe Asp Gly Ile Thr Asp Pro Val Tyr His Val Ser Tyr Gly Ile
        35                  40                  45

Val Leu Pro Gln Ala Thr Thr Ser Ser Glu Phe Ile Gly Glu Ile Val
    50                  55                  60

Ala Pro Leu Asp Ala Lys Trp Ile Gly Leu Ala Leu Gly Gly Ala Met
65                  70                  75                  80

Ile Gly Asp Leu Leu Ile Val Ala Trp Pro Asn Gly Asn Glu Ile Val
                85                  90                  95

Ser Ser Thr Arg Tyr Ala Thr Ala Tyr Gln Leu Pro Asp Val Tyr Ala
            100                 105                 110

Gly Pro Thr Ile Thr Thr Leu Pro Ser Ser Leu Val Asn Ser Thr His
        115                 120                 125

Trp Lys Phe Val Phe Arg Cys Gln Asn Cys Thr Ser Trp Glu Gly Gly
    130                 135                 140

Gly Gly Ile Asp Pro Thr Gly Thr Gly Val Phe Ala Trp Ala Tyr Ser
145                 150                 155                 160

Ser Val Gly Val Asp Asp Pro Ser Asp Pro Asn Thr Thr Phe Gln Glu
                165                 170                 175
```

```
His Thr Asp Phe Gly Phe Phe Gly Ile Asn Phe Pro Asp Ala Gln Asn
            180                 185                 190

Ser Asn Tyr Gln Asn Tyr Leu Gln Gly Asn Ala Gly Thr Pro Pro Pro
        195                 200                 205

Thr Ser Thr Pro Ser Gly Pro Thr Thr Thr Ser Lys Pro Thr Gly Pro
    210                 215                 220

Thr Ala Ser Ala Thr Pro Tyr Asp Tyr Ile Ile Val Gly Ala Gly Pro
225                 230                 235                 240

Gly Gly Ile Ile Ala Ala Asp Arg Leu Ser Glu Ala Gly Lys Lys Val
                245                 250                 255

Ile Leu Leu Glu Arg Gly Gly Pro Ser Thr Ala Glu Thr Gly Gly Thr
            260                 265                 270

Tyr Tyr Ala Pro Trp Ala Lys Ser Gln Asn Leu Thr Lys Phe Asp Ile
        275                 280                 285

Pro Gly Leu Phe Glu Ser Met Phe Thr Asp Pro Asn Pro Trp Trp Trp
    290                 295                 300

Cys Lys Asp Thr Asn Phe Phe Ala Gly Cys Leu Leu Gly Gly Gly Thr
305                 310                 315                 320

Ser Val Asn Gly Ala Leu Tyr Trp Leu Pro Ser Asp Ala Asp Phe Ser
                325                 330                 335

Thr Ala Asn Gly Trp Pro Thr Asn Trp Gly Asn His Ala Pro Tyr Thr
            340                 345                 350

Ser Lys Leu Lys Gln Arg Leu Pro Ser Thr Asp His Pro Ser Ala Asp
        355                 360                 365

Gly Asn Arg Tyr Leu Glu Gln Ser Ala Thr Val Val Ser Gln Leu Leu
    370                 375                 380

Gln Gly Gln Gly Tyr Gln Gln Ile Thr Ile Asn Asp Asn Pro Asp Tyr
385                 390                 395                 400

Lys Asp His Val Phe Gly Tyr Ser Ala Phe Asp Phe Ile Asn Gly Gln
                405                 410                 415

Arg Ala Gly Pro Val Ala Thr Tyr Phe Gln Thr Ala Ser Ala Arg Ser
            420                 425                 430

Asn Phe Val Tyr Lys Asp Tyr Thr Leu Val Ser Gln Val Leu Arg Asn
        435                 440                 445

Gly Ser Thr Ile Thr Gly Val Arg Thr Asn Asn Thr Ala Leu Gly Pro
    450                 455                 460

Asp Gly Ile Val Pro Leu Asn Pro Asn Gly Arg Val Ile Leu Ala Ala
465                 470                 475                 480

Gly Ser Phe Gly Thr Pro Arg Ile Leu Phe Gln Ser Gly Ile Gly Pro
                485                 490                 495

Thr Asp Met Ile Gln Thr Val Gln Ser Asn Pro Thr Ala Ala Ala Asn
            500                 505                 510

Leu Pro Pro Gln Ser Glu Trp Ile Asn Leu Pro Val Gly Gln Gly Val
        515                 520                 525

Ser Asp Asn Pro Ser Ile Asn Leu Val Phe Thr His Pro Ser Ile Asp
    530                 535                 540

Ala Tyr Glu Asn Trp Ala Asp Val Trp Ser Asn Pro Arg Pro Ala Asp
545                 550                 555                 560

Ala Gln Gln Tyr Leu Gln Ser Arg Ser Gly Val Phe Ala Gly Ala Ser
                565                 570                 575

Pro Lys Leu Asn Phe Trp Arg Ala Tyr Gly Gly Ser Asp Gly Lys Thr
            580                 585                 590
```

```
Arg Tyr Ala Gln Gly Thr Val Arg Pro Gly Ala Ala Ser Val Asn Thr
            595                 600                 605

Ser Val Ala Tyr Asn Ala Ser Gln Ile Phe Thr Ile Thr Val Tyr Leu
    610                 615                 620

Ser Glu Gly Ile Thr Ser Arg Gly Arg Leu Gly Val Asp Ala Ala Leu
625                 630                 635                 640

Asn Met Lys Ala Ile Thr Thr Pro Trp Leu Thr Asp Pro Val Asp Lys
                645                 650                 655

Thr Ile Leu Leu Gln Ala Leu His Asp Val Val Ser Asn Ile Asn Asn
            660                 665                 670

Val Pro Gly Leu Thr Leu Ile Thr Pro Asp His Thr Gln Thr Leu Glu
            675                 680                 685

Gln Tyr Val Ala Ala Tyr Asp Pro Ala Thr Met Cys Ser Asn His Trp
        690                 695                 700

Val Gly Ala Ala Lys Ile Gly Ser Ser Pro Ser Thr Ala Val Val Asp
705                 710                 715                 720

Glu Asn Thr Lys Val Phe Asn Thr Asp Asn Leu Phe Ile Val Asp Ala
                725                 730                 735

Ser Ile Ile Pro Ser Leu Pro Val Gly Asn Pro His Gly Ala Leu Met
            740                 745                 750

Ser Ala Ala Glu Gln Ala Ala Ala Lys Ile Leu Ala Leu Ala Gly Gly
        755                 760                 765

Pro

<210> SEQ ID NO 2
<211> LENGTH: 750
<212> TYPE: PRT
<213> ORGANISM: Pycnoporus cinnabarinus

<400> SEQUENCE: 2

Gln Val Ala Ala Pro Tyr Val Asp Ser Gly Asn Gly Phe Val Phe Asp
1               5                   10                  15

Gly Ile Thr Asp Pro Val Tyr His Val Ser Tyr Gly Ile Val Leu Pro
            20                  25                  30

Gln Ala Thr Thr Ser Ser Glu Phe Ile Gly Glu Ile Val Ala Pro Leu
        35                  40                  45

Asp Ala Lys Trp Ile Gly Leu Ala Leu Gly Gly Ala Met Ile Gly Asp
    50                  55                  60

Leu Leu Ile Val Ala Trp Pro Asn Gly Asn Glu Ile Val Ser Ser Thr
65                  70                  75                  80

Arg Tyr Ala Thr Ala Tyr Gln Leu Pro Asp Val Tyr Glu Gly Pro Thr
                85                  90                  95

Ile Thr Thr Leu Pro Ser Ser Leu Val Asn Ser Thr His Trp Lys Phe
            100                 105                 110

Val Phe Arg Cys Gln Asn Cys Thr Ser Trp Glu Gly Gly Gly Gly Ile
        115                 120                 125

Asp Pro Thr Gly Thr Gly Val Phe Ala Trp Ala Tyr Ser Ser Val Gly
    130                 135                 140

Val Asp Asp Pro Ser Asp Pro Asn Thr Thr Phe Gln Glu His Thr Asp
145                 150                 155                 160

Phe Gly Phe Phe Gly Ile Asn Phe Pro Asp Ala Gln Asn Ser Asn Tyr
                165                 170                 175

Gln Asn Tyr Leu Gln Gly Asn Ala Gly Thr Pro Pro Thr Ser Thr
            180                 185                 190
```

```
Pro Ser Gly Pro Thr Thr Ser Lys Pro Thr Gly Pro Thr Ala Ser
            195                 200                 205
Ala Thr Pro Tyr Asp Tyr Ile Ile Val Gly Ala Gly Pro Gly Gly Ile
210                 215                 220
Ile Ala Ala Asp Arg Leu Ser Glu Ala Gly Lys Lys Val Ile Leu Leu
225                 230                 235                 240
Glu Arg Gly Gly Pro Ser Thr Ala Glu Thr Gly Gly Thr Tyr Tyr Ala
                245                 250                 255
Pro Trp Ala Lys Ser Gln Asn Leu Thr Lys Phe Asp Ile Pro Gly Leu
            260                 265                 270
Phe Glu Ser Met Phe Thr Asp Pro Asn Pro Trp Trp Trp Cys Lys Asp
            275                 280                 285
Thr Asn Phe Phe Ala Gly Cys Leu Leu Gly Gly Thr Ser Val Asn
    290                 295                 300
Gly Ala Leu Tyr Trp Leu Pro Ser Asp Ala Asp Phe Ser Thr Ala Asn
305                 310                 315                 320
Gly Trp Pro Thr Ser Trp Gly Asn His Ala Pro Tyr Thr Ser Lys Leu
                325                 330                 335
Lys Gln Arg Leu Pro Ser Thr Asp His Pro Ser Thr Asp Gly Lys Arg
            340                 345                 350
Tyr Leu Glu Gln Ser Ala Thr Val Val Ser Gln Leu Leu Gln Gly Gln
            355                 360                 365
Gly Tyr Gln Gln Ile Thr Ile Asn Asp Asn Pro Asp Ser Lys Asp His
            370                 375                 380
Val Phe Gly Tyr Ser Ala Phe Asp Phe Ile Asn Gly Gln Arg Ala Gly
385                 390                 395                 400
Pro Val Ala Thr Tyr Phe Gln Thr Ala Ser Ala Arg Ser Asn Phe Val
                405                 410                 415
Tyr Lys Asp Phe Thr Leu Val Ser Gln Val Leu Arg Asn Gly Ser Thr
            420                 425                 430
Ile Thr Gly Val Arg Thr Asn Asn Thr Ala Leu Gly Pro Asp Gly Ile
            435                 440                 445
Val Pro Leu Asn Pro Asn Gly Arg Val Ile Leu Ala Ala Gly Ser Phe
450                 455                 460
Gly Thr Pro Arg Ile Leu Phe Gln Ser Gly Ile Gly Pro Thr Asp Met
465                 470                 475                 480
Ile Gln Thr Val Gln Ser Asn Pro Thr Ala Ala Asn Leu Pro Pro
            485                 490                 495
Glu Ser Glu Trp Ile Asn Leu Pro Val Gly Gln Gly Val Ser Asp Asn
                500                 505                 510
Pro Ser Ile Asn Leu Val Phe Thr His Pro Ser Ile Asp Ala Tyr Glu
            515                 520                 525
Asn Trp Ala Asp Val Trp Ser Asn Pro Arg Pro Ala Asp Ala Gln Gln
            530                 535                 540
Tyr Leu Gln Ser Arg Ser Gly Val Phe Ala Gly Ala Ser Pro Lys Leu
545                 550                 555                 560
Asn Phe Trp Arg Ala Tyr Gly Gly Ser Asp Gly Lys Thr Arg Tyr Ala
                565                 570                 575
Gln Gly Thr Val Arg Pro Gly Ala Ala Ser Val Asn Thr Ser Val Ala
            580                 585                 590
Tyr Asn Ala Ser Gln Ile Phe Thr Ile Thr Val Tyr Leu Ser Glu Gly
            595                 600                 605
Ile Thr Ser Arg Gly Arg Leu Gly Val Asp Ala Ala Leu Asn Met Lys
```

Ala Ile Thr Thr Pro Trp Leu Thr Asp Pro Val Asp Lys Thr Ile Leu
625                 630                 635                 640

Leu Gln Ala Leu His Asp Val Val Ser Asn Ile Asn Asn Val Pro Gly
            645                 650                 655

Leu Thr Leu Ile Thr Pro Asp His Thr Gln Thr Leu Glu Gln Tyr Val
        660                 665                 670

Ala Ala Tyr Asp Pro Ala Thr Met Cys Ser Asn His Trp Val Gly Ala
    675                 680                 685

Ala Lys Ile Gly Ser Ser Pro Ser Thr Ala Val Val Asp Glu Asn Thr
690                 695                 700

Lys Val Phe Asn Thr Asp Asn Leu Phe Ile Val Asp Ala Ser Ile Ile
705                 710                 715                 720

Pro Ser Leu Pro Val Gly Asn Pro His Gly Ala Leu Met Ser Ala Ala
            725                 730                 735

Glu Gln Ala Ala Ala Lys Ile Leu Ala Leu Ala Gly Gly Pro
            740                 745                 750

<210> SEQ ID NO 3
<211> LENGTH: 26
<212> TYPE: DNA
<213> ORGANISM: Artificial sequence
<220> FEATURE:
<223> OTHER INFORMATION: forward primer cdhF designed from P.
      cinnabarinus I-937 cdh gene (NCBI AF081574)

<400> SEQUENCE: 3
tagaatccca agtggcagcg ccatac                                        26

<210> SEQ ID NO 4
<211> LENGTH: 28
<212> TYPE: DNA
<213> ORGANISM: Artificial sequence
<220> FEATURE:
<223> OTHER INFORMATION: reverse primer cdhR designed from P.
      cinnabarinus I-937 cdh gene (NCBI AF081574)

<400> SEQUENCE: 4
tatctagacc aggacctccc gcaagggc                                      28

<210> SEQ ID NO 5
<211> LENGTH: 19
<212> TYPE: DNA
<213> ORGANISM: Artificial sequence
<220> FEATURE:
<223> OTHER INFORMATION: cdhint primer

<400> SEQUENCE: 5
cgacgcccag aactcgaac                                                19

<210> SEQ ID NO 6
<211> LENGTH: 41
<212> TYPE: DNA
<213> ORGANISM: Artificial sequence
<220> FEATURE:
<223> OTHER INFORMATION: forward primer PaGH61BF designed from P.
      anserina S mat+ GH61B gene (NCBI gene id: CAP68375.1)

<400> SEQUENCE: 6
aggggtatct ctcgagaaaa gacattccac cttccaacag c                       41

<210> SEQ ID NO 7

```
<211> LENGTH: 36
<212> TYPE: DNA
<213> ORGANISM: Artificial sequence
<220> FEATURE:
<223> OTHER INFORMATION: reverse primer PaGH61B R designed from P.
      anserina S mat+ GH61B gene (NCBI gene id: CAP68375.1)

<400> SEQUENCE: 7 gagttttgt tctagaccca cgcactggtg atacca                               36

<210> SEQ ID NO 8
<211> LENGTH: 38
<212> TYPE: DNA
<213> ORGANISM: Artificial sequence
<220> FEATURE:
<223> OTHER INFORMATION: forward primer PaGH61A F designed from P.
      anserina S mat+ gh61A gene (GenBank: CAP73254.1)

<400> SEQUENCE: 8
aggggtatct ctcgagaaaa gacacggcca cgtctccc                             38

<210> SEQ ID NO 9
<211> LENGTH: 38
<212> TYPE: DNA
<213> ORGANISM: Artificial sequence
<220> FEATURE:
<223> OTHER INFORMATION: Reverse primer PaGH61A R designed from P.
      anserina S mat+ gh61A gene (GenBank: CAP73254.1)

<400> SEQUENCE: 9 gagttttgt tctagaccga tgcactggct gtagtaag                              38

<210> SEQ ID NO 10
<211> LENGTH: 43
<212> TYPE: DNA
<213> ORGANISM: Artificial sequence
<220> FEATURE:
<223> OTHER INFORMATION: forward primer PaGH61E F designed from P.
      anserina S mat+ GH61E gene (GenBank: CAP61476.1)

<400> SEQUENCE: 10
aggggtatct ctcgagaaaa gacactccat cttccaaaag gtg                       43

<210> SEQ ID NO 11
<211> LENGTH: 33
<212> TYPE: DNA
<213> ORGANISM: Artificial sequence
<220> FEATURE:
<223> OTHER INFORMATION: Reverse primer PaGH61E R designed from P.
      anserina S mat+ GH61E gene (GenBank: CAP61476.1)

<400> SEQUENCE: 11 gagttttgt tctagacctg tactaccgcc tgg                                   33

<210> SEQ ID NO 12
<211> LENGTH: 351
<212> TYPE: PRT
<213> ORGANISM: Podospora anserina

<400> SEQUENCE: 12

Met Ser Asn Lys Ala Ala Thr Leu Leu Ala Ala Leu Ser Gly Ala Ala
 1               5                  10                  15

Leu Val Ala Ala His Gly His Val Ser His Ile Ile Val Asn Gly Val
                20                  25                  30

Tyr Tyr Gln Asn Tyr Asp Pro Thr Thr His Phe Tyr Gln Pro Asn Pro
            35                  40                  45
```

-continued

Pro Thr Val Ile Gly Trp Ser Ala Leu Gln Gln Asp Asn Gly Phe Val
 50                   55                  60

Glu Pro Asn Asn Phe Gly Thr Thr Asp Ile Ile Cys His Lys Ser Ala
 65                  70                  75                  80

Ala Pro Gly Gly Gly Ser Ala Thr Val Asn Ala Gly Asp Lys Ile Ser
                 85                  90                  95

Ile Val Trp Thr Pro Glu Trp Pro Ser His Ile Gly Pro Val Ile
             100                 105                 110

Asp Tyr Leu Ala Asn Cys Asn Gly Pro Cys Glu Thr Val Asp Lys Thr
             115                 120                 125

Ser Leu Arg Trp Phe Lys Ile Gly Gly Ala Gly Tyr Asn Pro Asn Thr
        130                 135                 140

Arg Thr Trp Ala Ala Asp Asp Leu Arg Ala Asn Gly Asn Ser Trp Leu
145                 150                 155                 160

Val Gln Ile Pro Ala Asp Leu Lys Ala Gly Asn Tyr Val Leu Arg His
                165                 170                 175

Glu Ile Ile Ala Leu His Gly Gly Ser Ser Pro Asn Gly Ala Gln Ala
            180                 185                 190

Tyr Pro Gln Cys Leu Asn Leu Arg Ile Val Gly Asn Gly Asn Asn Ser
        195                 200                 205

Pro Ala Gly Val Ala Gly Thr Ser Leu Tyr Arg Ala Asn Asp Ala Gly
210                 215                 220

Ile Leu Phe Asn Pro Tyr Val Ala Ser Pro Asn Tyr Pro Val Pro Gly
225                 230                 235                 240

Pro Ala Leu Ile Ala Gly Ala Val Ser Ser Ile Pro Gln Ser Lys Ser
                245                 250                 255

Thr Ala Thr Arg Thr Ala Ser Ala Thr Leu Pro Gly Ala Pro Val Val
            260                 265                 270

Thr Pro Thr Ala Gly Pro Val Val Thr Thr Ser Ser Ala Pro Val Val
        275                 280                 285

Gln Pro Pro Thr Thr Thr Leu Val Thr Val Thr Ser Ala Pro Ala Thr
290                 295                 300

Ser Ala Ala Pro Ala Pro Thr Gly Gly Ala Gly Val Ala Pro Lys Trp
305                 310                 315                 320

Gly Gln Cys Gly Gly Asn Gly Trp Thr Gly Pro Thr Val Cys Ala Ser
                325                 330                 335

Gly Ser Thr Cys Thr Val Leu Asn Pro Tyr Tyr Ser Gln Cys Ile
            340                 345                 350

<210> SEQ ID NO 13
<211> LENGTH: 327
<212> TYPE: PRT
<213> ORGANISM: Podospora anserina

<400> SEQUENCE: 13

Met Lys Ser Phe Thr Ala Thr Ala Leu Ala Ala Leu Leu Ala Gln Gln
 1               5                  10                  15

Ala Ala Ala His Ser Thr Phe Gln Gln Leu Trp Val Asp Gly Thr Asp
                20                  25                  30

Phe Gly Ser Gln Cys Ala Arg Leu Pro Gln Ser Asn Ser Pro Ile Thr
            35                  40                  45

Asn Tyr Asn Ser Asn Asp Met Arg Cys Asn Ile Ile Gly Thr Arg Pro
         50                  55                  60

Gln Val Lys Cys Pro Val Arg Ala Gly Gly Thr Val Thr Val Glu Met

His Ala Gln Asn Gly Asp Arg Ser Cys Ser Gln Glu Ala Ile Gly Gly
65                  70                  75                  80

Ala His His Gly Pro Val Ser Val Tyr Leu Thr Lys Val Ser Asp Ala
                85                  90                  95

Leu Thr Ala Asp Gly Ser Thr Gly Trp Phe Lys Ile Phe Asp Asp Gly
            100                 105                 110

Trp Arg Lys Asn Pro Ser Gly Arg Val Gly Asp Asp Phe Trp Gly
        115                 120                 125

Thr Lys Asp Leu Asn Ala Cys Cys Gly Lys Met Asn Val Lys Ile Pro
145                 150                 155                 160

Ser Asp Ile Pro Ser Gly Asp Tyr Leu Leu Arg Ala Glu Ala Ile Ala
                165                 170                 175

Leu His Ala Ala Gly Gly Ala Gly Gly Ala Gln Pro Tyr Met Thr Cys
            180                 185                 190

Tyr Gln Ile Thr Val Ser Gly Gly Ser Ala Ser Pro Pro Thr Val
        195                 200                 205

Ser Ile Pro Gly His Phe Lys Ala Ser Asp Pro Gly Val Gln Val Asn
210                 215                 220

Ile His Gly Ala Met Thr Asn Tyr Val Ile Pro Gly Pro Ala Val Tyr
225                 230                 235                 240

Ala Gly Gly Ser Thr Lys Val Ala Gly Ser Ala Cys Ser Gly Cys Glu
                245                 250                 255

Ala Thr Cys Ala Val Gly Ser Ser Pro Thr Thr Ser Leu Thr Pro Pro
            260                 265                 270

Val Ser Thr Ser Thr Pro Ala Pro Gly Asn Gly Gly Gly Ser Pro
        275                 280                 285

Gly Gly Cys Thr Val Gln Lys Tyr Gly Gln Cys Gly Gly Gln Gly Tyr
            290                 295                 300

Thr Gly Cys Thr Thr Cys Ala Ala Gly Ser Thr Cys Asn Thr Thr Asn
305                 310                 315                 320

Gln Trp Tyr His Gln Cys Val
                325

<210> SEQ ID NO 14
<211> LENGTH: 370
<212> TYPE: PRT
<213> ORGANISM: Podospora anserina

<400> SEQUENCE: 14

Met Lys Ala Phe Thr Leu Val Ser Leu Ala Ala Ser Val Ser Ala His
1               5                   10                  15

Ser Ile Phe Gln Lys Val Ser Val Asn Gly Val Asp Gln Gly Gln Leu
                20                  25                  30

Lys Gly Val Arg Ala Pro Tyr Ser Asn Phe Pro Ile Glu Asn Val Asn
            35                  40                  45

His Pro Asp Phe Ala Cys Asn Thr Asn Ile Gln Leu Arg Asp Asn Thr
        50                  55                  60

Val Ile Lys Val Pro Ala Gly Ala Arg Val Gly Ala Trp Trp Gly His
65                  70                  75                  80

Glu Ile Gly Gly Ala Ala Gly Pro Asn Asp Pro Asp His Pro Ile Ala
                85                  90                  95

Ala Ser His Lys Gly Pro Ile Gln Val Tyr Leu Ala Lys Val Asn Asn
            100                 105                 110

-continued

```
Ala Ala Asn Ala Gly Thr Ser Gly Leu Gln Trp Phe Lys Val Ala Glu
        115                 120                 125

Gln Gly Leu Asn Asn Gly Val Trp Ala Val Asp Asn Met Ile Ser Asn
    130                 135                 140

Gly Gly Trp His Tyr Phe Asp Met Pro Ser Cys Val Ala Pro Gly His
145             150                 155                 160

Tyr Leu Met Arg Val Glu Leu Leu Ala Leu His Ser Ala Ser Val Arg
            165                 170                 175

Gly Ala Ala Gln Phe Tyr Met Glu Cys Ala Gln Ile Glu Ile Thr Gly
            180                 185                 190

Ser Gly Thr Asn Thr Gly Ser Asn Phe Val Ser Phe Pro Gly Ala Tyr
    195                 200                 205

Thr Ala Asp His Pro Gly Ile Leu Val Ser Ile Tyr Asp Leu Gln Gly
    210                 215                 220

Arg Pro Thr Asn Gly Gly Arg Pro Tyr Thr Ile Pro Gly Pro Ala Pro
225                 230                 235                 240

Leu Thr Cys Ser Gly Gly Ser Asn Pro Asn Pro Gln Pro Gln Pro Thr
            245                 250                 255

Ser Ala Ala Pro Asn Pro Gln Pro Thr Gly Gly Asn Gly Gly Gly Ala
            260                 265                 270

Gly Ala Pro Leu Tyr Gly Gln Cys Gly Gly Gln Gly Tyr Thr Gly Pro
    275                 280                 285

Thr Thr Cys Ala Gln Gly Thr Cys Val Ala Ser Asn Gln Trp Tyr Ser
    290                 295                 300

Met Leu Ser Pro Leu Ser Phe Phe Ala Ser His Met Leu Thr Cys Leu
305                 310                 315                 320

Ser Ser Arg Pro Val Pro Pro Ile Asn Val Ser Met Arg Leu Gly Lys
            325                 330                 335

Gly His Glu His Glu Arg Arg Arg Ile Asn Thr Asn Lys His Leu Ile
            340                 345                 350

Phe Thr Cys Ile Tyr Phe Ser Ile Leu Pro Pro Asp Ile Pro Gly Gly
            355                 360                 365

Ser Thr
    370
```

COMPOSITIONS COMPRISING CELLOBIOSE DEHYDROGENASE FROM *PYCNOPORUS CINNABARINUS* AND THEIR USE FOR THE DEGRADATION OF LIGNOCELLULOSIC BIOMASS

The present patent application claims priority from the provisional patent application U.S. 61/504,426 filed on Jul. 5, 2011 which whole content is herein incorporated by reference.

FIELD OF THE INVENTION

The present invention relates to enzyme compositions comprising at least a cocktail of cellulases from *Trichoderma reesei*, and an enzymatic cocktail from *Pycnoporus cinnabarinus* comprising a cellobiose dehydrogenase (CDH) or a recombinant cellobiose dehydrogenase (CDH) from *Pycnoporus cinnabarinus*, preferably also comprising a Family 61 glycoside hydrolase from *Podospora anserina* and also relates to methods for degrading a lignocellulosic biomass, for producing a fermentation product, for producing gluconic acid, xylonic acid and/or xylobionic acid, for enhancing the production of gluconic acid, xylonic acid and/or xylobionic acid or for increasing the yield of sugars from a lignocellulosic biomass.

BACKGROUND

Lignocellulose is the most abundant component of biomass, comprising around half of plant matter produced by photosynthesis and representing the most plentiful renewable organic resource in the soil. It contains mainly three types of polymer: cellulose, hemicellulose and lignin. Each of these is strongly intermeshed and chemically bonded by non-covalent forces and by covalent crosslinkages. Cellulose accounts for up to 45% of total wood lignocellulose dry weight. It is a linear polymer composed of D-glucose subunits linked by β-1,4-glycosidic bonds forming long chains (or elemental fibrils) linked together by hydrogen bonds and van der Waals forces. Hemicelluloses are a heteropolymers representing, 15-35% of plant biomass and containing pentoses (β-D-xylose, α-L-arabinose), hexoses (β-D-mannose, β-D-glucose, α-D-galactose) and/or uronic acids. Lignin is composed of phenylpropane units joined together by different types of linkages. Lignin is linked to both hemicellulose and cellulose, coating them and forming a physical barrier between degrading enzymes and the plant cell wall.

In natural environments, cellulolytic microorganisms secrete enzymes that function synergistically, in association with the microorganism or independently. Although it is not fully known how many enzymes are involved in cell wall deconstruction, three general categories of enzymes are considered necessary to hydrolyze native cell wall materials: cellulases, hemicellulases and accessory enzymes such as hemicellulose debranching enzymes, phenolic acid esterase, and possibly lignin degrading and modifying enzymes. Three classes of enzymes act synergistically to hydrolyse cellulose: endo-β-1,4-glucanases, cleaving cellulose into shorter chains, cellobiohydrolases releasing cellobiose from the ends of the polymer, further cleaved into two glucose molecules by β-glucosidases. By loosening hemicellulose layers, hemicellulases presumably expose the cellulose fibers in the plant cell wall matrix, making them more accessible to hydrolysis. The efficient degradation of this polymer requires the concerted action of a range of enzymes working synergistically such as xylanases, β-mannanases, β-xylosidases, α-L-arabinofuranosidases and esterases. Lignin biodegradation by white-rot fungi is an oxidative process assisted by key enzymes such as phenoloxidase (laccase) and lignin-modifying peroxidase (lignin peroxidase, manganese peroxidase and versatile peroxidase).

The main industrial source of cellulases and hemicellulases is the mesophilic soft-rot fungus *T. reesei* (teleomorph *Hypocrea jecorina*), valued for the high protein secretion capacity of its mutant strains obtained by random mutagenesis (producing up to 100 g of extracellular protein per liter of culture).

In the context of biorefinery, chemical and structural features of biomass affect enzyme accessibility and activity, thereby affecting conversion costs. Pretreatment of lignocellulosic biomass aims to make the cellulose accessible to hydrolytic enzymes by altering the lignocellulosic cell wall. Pretreatment increases the accessible surface area, cellulose decrystallinization, partial cellulose depolymerization, hemicellulose and/or lignin solubilization, and the modification of the lignin structure.

Among fungal classes, basidiomycetes are known to be efficient degraders of cellulose, many species growing on dead wood or litter. The lignocellulolytic system of basidiomycetes has been studied intensively in the last decades. Genome sequencing and proteomic tools are often used, but the cellulolytic system is still not completely understood, especially the oxidative part of this system.

Cellobiose dehydrogenases (CDH; classified according to the enzyme nomenclature as E.C. 1.1.99.18; cellobiose: [acceptor] 1-oxidoreductase) are extracellular fungal hemoflavoenzymes produced by many white-rot fungi including *Trametes versicolor, Phanerochaete chrysosporium, Ceriporiopsis subvermispora* and *P. cinnabarinus* (Moukha, S. M. et al, 1999, Gene, vol. 234, pp: 23-33). CDH are also produced by the brown-rot fungus *Coniophora puteana* and the soft-rot fungus *Humicola insolens*. More recently, CDH from the ascomycetes *Myriococcum thermophilum* and *Neurospora crassa* were cloned and successfully expressed in *Pichia pastoris*. CDH are monomeric enzymes consisting of two prosthetic groups, a heme and a flavin domain. The heme-binding domain in the N-terminal position contains a cytochrome b-type heme which presents an unusual heme binding by Met/His ligation. The flavin domain in C-terminal binds FAD non-covalently and is classified as a member of the glucose-methano-choline family of oxidoreductases. These two regions are separated by a Thr-Ser-rich long linker region. The flavoprotein domain of CDH catalyzes two-electron oxidation of cellobiose and more generally cellodextrines, mannodextrines and lactose to corresponding lactones using electron acceptors such as dioxygen, quinones, phenoxyradicals and others. Also, one-electron transfer occurs. Heme is implicated in one internal electron transfer to FAD or another electron acceptor such as $Fe^{3+}$.

Among oxidoreductases, laccases have been the most intensively studied, while CDHs are less well-researched. Only a few CDHs have been studied such as the CDH of *P. chrysosporium*, of *Sclerotium (Athelia) rolfsii*, or of *Monilia* sp.

Although the role of CDHs is still unclear, it is established that CDHs are produced in cellulolytic conditions and are involved in cellulose and lignin degradation. CDHs have been shown to bind cellulose by two different structures depending on species: a long aromatic-rich region for *P. chrysosporium* and *P. cinnabarinus* or a cellulose-binding domain for ascomycetes and soft-rot fungi, similar to that observed for cellulases (Henriksson G. et al, 1997, Journal of Biochemistry, vol. 324, pp: 833-838).

Their involvement in many reactions has been demonstrated, e.g. reduction of quinones, inhibition of phenol radical repolymerization, production of hydrogen peroxide, enhancement of manganese peroxidase turn-over and one of the most often cited reactions, the production of hydroxyl radicals by a Fenton-type reaction, which may participate in the degradation of cellulose, lignin and xylan. CDHs are known to enhance the action of cellulases on crystalline cellulose and also to degrade wood components, but their role in complex lignocellulosic substrate degradation has never been investigated.

In 2008, various compositions comprising *T. reesei* cellulases combined with CDHs from different origins were tested in the International application WO2010/080532 which demonstrated that, unless to add a Family 61 glycoside hydrolase, each of the tested compositions comprising *T. reesei* cellulases combined with CDHs from different origins led to an inhibition of the crystalline cellulose degradation, therefore not enabling an improved degradation of lignocellulosic biomass.

SUMMARY OF THE INVENTION

Cellobiose dehydrogenase (CDH) is an extracellular hemoflavoenzyme produced by lignocellulose-degrading fungi including *Pycnoporus cinnabarinus*. The inventors investigated the cellulolytic system of *P. cinnabarinus*, focusing on the involvement of CDH in the deconstruction of lignocellulosic biomass in order to provide new cocktail compositions and to improve various processes for lignocellulosic biomass degradation.

Analysis of the *Pycnoporus cinnabarinus* secretome has shown that CDH is a key enzyme for cellulose hydrolysis. In view of its interest in saccharification processes, the inventors heterologously expressed the *P. cinnabarinus* CDH in *Pichia pastoris*. The recombinant enzyme was characterized in depth and assayed for its ability to degrade native and pre-treated substrates as a supplement to commercial *Trichoderma reesei* cocktail.

The inventors surprisingly demonstrated that an enzyme cocktail of *T. reesei* combined with a *P. cinnabarinus* CDH enabled to improve the lignocellulosic degradation, on the contrary to the results observed with different CDHs in WO2010/080532. The differences of results could be related to the structures of the CDHs as CDH from ascomycetes and soft-rot fungi comprise a cellulose-binding domain which could be implicated in the inhibition of biomass degradation on the contrary to the *P. cinnabarinus* and *P. chrysosporium* CDHs which do not contain such a cellulose-binding domain but a long aromatic-rich region as disclosed previously.

First, *P. cinnabarinus* growth conditions were optimized for CDH production. Following growth under cellulolytic conditions, the main components secreted were cellulases, xylanases, CDH and laccase.

To investigate the contribution of *P. cinnabarinus* secretome in saccharification processes, the *Trichoderma reesei* enzymatic cocktail was supplemented with β-glucosidases from *Aspergillus niger* and with the *P. cinnabarinus* secretome in a first set of experiment. A significant enhancement of the degradation of crude wheat straw and acid steam-exploded wheat straw was observed with:
(i) the production of a large amount of gluconic acid derived from C6 sugars correlated with a slight decrease in glucose yield,
(ii) yield in C5 sugars from hemicelluloses, consistent with the lignin degradation effect of the secretome, and
(iii) increased overall degradation of the lignocellulosic material.

Similar results were observed to a lesser extent on pretreated wheat straw. Therefore, the use of *P. cinnabarinus* secretome with a *Trichoderma reesei* enzymatic cocktail supplemented with β-glucosidases from *Aspergillus niger* enables the production of a large amount of gluconic acid coming from cellulose hydrolysis and an increased hemicellulose degradation giving increased overall degradation of the lignocellulosic material.

*P. cinnabarinus* CDH was heterologously expressed in *Pichia pastoris* to obtain large amounts of pure enzyme. In a bioreactor, the recombinant CDH (rCDH) expression level reached 7800 U·l$^{-1}$, the highest reported to date. rCDH exhibited values of biochemical parameters similar to those of the natural enzyme, and was able to bind cellulose despite the absence of a carbohydrate-binding module (CBM). Following supplementation of purified rCDH to *T. reesei* enzymatic cocktail, formation of gluconic acid coming from cellulose degradation and increased hemicellulose degradation were observed, even gluconic acid and C5 sugar hemicellulose production was enhanced for 10 U CDH supplementation with no decrease in glucose yield, thus confirming the previous results observed with *P. cinnabarinus* secretome. The various results of the inventors therefore point the synergy between CDH and cellulases for degradation of lignocellulosic biomass.

Moreover, the inventors demonstrated the stability to relatively high temperatures (above 55° C.) of the recombinant CDH enzyme from *P. cinnabarinus* expressed in *Pichia pastoris*. Such stability therefore allows the use of a recombinant CDH for liquefaction of suspension of at least 20% dry weight in order to obtain sugar solution yielding high ethanol concentrations (above 8% v/v).

In addition, the supplementation with β-glucosidase leads to a greater production of gluconic acid and the supplementation of *T. reesei* secretome by CDH increases the overall degradation of lignocellulose and produces appreciable amounts of gluconic acid. Gluconic acid and its derivatives such as sodium gluconate support a wide range of applications. Production of gluconic acid from raw plant material could have economic advantages. Global production of gluconic acid is estimated to be in the range 50,000-100,000 ton/per year, and this metabolite can be used in several industrial processes including textile dyeing, food additives, detergents, cosmetics and pharmaceuticals.

The inventors demonstrated that CDH plays a key role in the cellulolytic system of *P. cinnabarinus*, thus offering an attractive tool for biotechnological applications such as saccharification process enhancement, gluconic acid production from lignocellulosic biomass and ethanol production especially when combined with an enzymatic cocktail from *T. reesei* with (β-glucosidase.

Therefore, a first aspect of the invention concerns a composition comprising at least:
a) An enzyme cocktail of cellulases from *Trichoderma reesei*, and
b) An enzyme cocktail from *Pycnoporus cinnabarinus* comprising a cellobiose dehydrogenase (CDH), or
c) a recombinant cellobiose dehydrogenase from *Pycnoporus cinnabarinus*.

Another aspect of the invention concerns a method for degrading a lignocellulosic biomass, wherein said method comprises a step of treating said lignocellulosic biomass with a composition according to the invention as disclosed previously.

Another aspect of the invention concerns a method for producing a fermentation product from a lignocellulosic biomass, said method comprising the following steps:

a) Liquefaction of a lignocellulosic biomass by using a composition according to the invention in order to obtain a liquefied product having a dry weight above 20%, b) Saccharification of the liquefaction product obtained from step a) with an enzyme cocktail, c) Fermentation of the saccharification product obtained from step b) by using a fermenting microorganism.

Another aspect of the invention concerns a method for producing gluconic acid, xylonic acid and/or xylobionic acid from a lignocellulosic biomass, wherein said method comprises the following steps:

a) Liquefaction of a lignocellulosic biomass by using a composition according to the invention as defined previously in order to obtain a liquefied product having a dry weight of at least 20%, b) Saccharification of the liquefaction product obtained from step a) with an enzyme cocktail.

Another aspect of the invention concerns a method for enhancing the production of gluconic acid, xylonic acid and/or xylobionic acid from a lignocellulosic biomass, wherein said method comprises the following steps:

a) Liquefaction of a lignocellulosic biomass by using a composition according to the invention in order to obtain a liquefied product having a dry weight of at least 20%, b) Saccharification of the liquefaction product obtained from step a) with an enzyme cocktail.

Another aspect of the invention concerns a method for enhancing the production of sugars from a lignocellulosic biomass, wherein said method comprises the following steps:

a) Liquefaction of a lignocellulosic biomass by using a composition according to the invention in order to obtain a liquefied product having a dry weight of at least 20%, b) Saccharification of the liquefaction product obtained from step a) with an enzyme cocktail.

Another aspect of the invention concerns the use of a recombinant cellobiose dehydrogenase from *Pycnoporus cinnabarinus* under high temperatures, preferably under temperatures comprised between 55-90° C.

DESCRIPTION OF THE INVENTION

Figure 1:
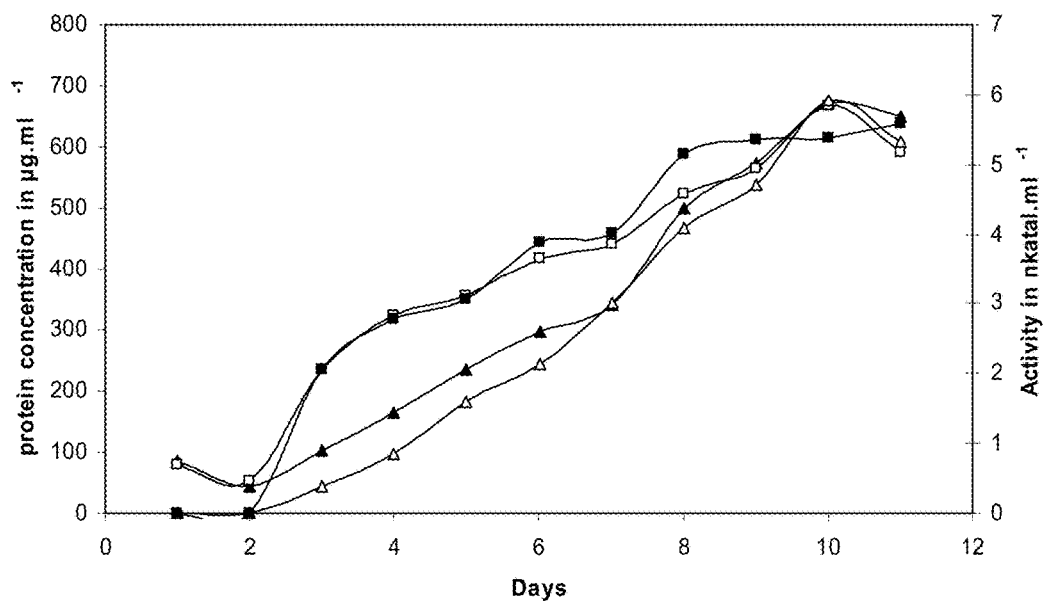
FIG. 1. Comparison of CDH production (▲ and ∆) and protein concentration (■ and □) in the culture of *P. cinnabarinus* ss3 using two different types of celluloses: cellulose medium fiber (open symbols) and cellulose CC 41 (solid symbols).

1—Abbreviation List
CDH, cellobiose dehydrogenase;
CMC, carboxymethylcellulose; DCPIP, 2,6-dichlorophenol indophenol;
ABTS, 2,2'-azino-bis-(3-ethylbenzthiazoline-6-sulfonic acid);
pNP, para-nitrophenol;
DNS, 3,5-dinitrosalicylic acid; cyt c, cytochrome c;
CBM, carbohydrate binding module;
rCDH, recombinant cellobiose dehydrogenase.

2—Definitions

The term "secretome" as used herein refers to the totality of the proteins which are released by a cell, a tissue or an organism. Methods for recovering the secretome of a cell, a tissue or an organism are easily known by a person skilled in the art.

The term "cellobiose dehydrogenase" is defined herein as a cellobiose:acceptor 1-oxidoreductase (classified according to the enzyme nomenclature as E. C. 1.1.99.18) that catalyzes the conversion of cellobiose in the presence of an acceptor to cellobiono-1,5-lactone and a reduced acceptor. 2,6-Dichloroindophenol can act as acceptor, as can iron, especially $Fe(SCN)_3$, molecular oxygen, ubiquinone, or cytochrome C, and likely many other polyphenols. Substrates of the enzyme include cellobiose, cello-oligosaccharides, lactose, and D-glucosyl-1,4-[beta]-D-mannose, glucose, maltose, mannobiose, thiocellobiose, galactosylmannose, xylobiose, xylose. Electron donors are preferably beta-1-4 dihexoses with glucose or mannose at the reducing end, though alpha-1-4 hexosides, hexoses, pentoses, and beta-1-4 pentomers have also been shown to act as substrates for these enzymes (Henriksson et al, 1998, Protein Structure and Molecular Enzymology; 1383: 48-54; Schou et al, 1998, Biochem. J. 330: 565-571).

The 3-dimensional structure of cellobiose dehydrogenase features two globular domains, each containing one of two cofactors: a heme or a flavin. The active site lies at a cleft between the two domains. The catalytic cycle of cellobiose dehydrogenase follows an ordered sequential mechanism. Oxidation of cellobiose occurs via 2-electron transfer from cellobiose to the flavin, generating cellobiono-1,5-lactone and reduced flavin. The active FAD is regenerated by electron transfer to the heme group, leaving a reduced heme. The native state heme is regenerated by reaction with the oxidizing substrate at the second active site. The oxidizing substrate is preferentially iron ferricyanide, cytochrome C, or an oxidized phenolic compound such as dichloroindophenol (DCIP), a substrate commonly used for colorimetric assays. Metal ions and $O_2$ are also substrates, but for most cellobiose dehydrogenases the reaction rate for these substrates is several orders of magnitude lower than that observed for iron or organic oxidants. Following cellobionolactone release, the product may undergo spontaneous ring-opening to generate cellobionic acid (Hallberg et al., 2003, J. Biol. Chem. 278: 7160-7166).

The term "recombinant cellobiose dehydrogenase" as used herein refers to a cellobiose dehydrogenase produced by a host organism through the expression of a recombinant nucleic acid molecule introduced into said host organism and encoding a cellobiose dehydrogenase. In particular embodiments, the cellobiose dehydrogenase is produced by any recombinant techniques known from any skilled in the art.

The term "Family 61 glycoside hydrolase" or "Family GH61" is defined herein as a polypeptide falling into the glycoside hydrolase Family 61 according to Henrissat B. et al (1991, Biochem. J. 280: 309-316) and Henrissat B., and Bairoch A. (1996, Biochem. J. 316: 695-696). Presently, Henrissat lists the GH61 Family as unclassified indicating that properties such as mechanism, catalytic nucleophile/base, and catalytic proton donors are not known for polypeptides belonging to this family.

The term "Lignocellulosic biomass" refers to material derived from plants or other organisms in which carbohydrate content is substantially lignocellulose constituted of cellulose, hemicellulose and more than 5% lignin. Lignin is a complex aromatic network formed by polymerisation of phenyl propane and comprising monomers including: p-coumaryl alcohol, coniferyl alcohol and sinapyl alcohol, typically linked through arylglyceryl-[beta]-aryl ether bonds.

The term Lignocellulosic biomass as used herein includes processed materials, such as papers having more than 5% lignin, as well as primarily natural materials, such as agricultural wastes.

Lignocellulosic biomass will typically comprise water content. A mixture of water and/or other agents and/or solvents comprising lignocellulosic biomass as the predominant solid component can also be referred to as "a" lignocellulosic biomass within the meaning of the term as used.

In a preferred embodiment, a lignocellulosic biomass according to the invention is selected in the group comprising herbaceous material, agricultural residues, forestry residues, municipal solid wastes, waste paper, pulp and paper mill residues, or any combination thereof.

In a still preferred embodiment, a lignocellulosic biomass according to the invention is selected in a group comprising corn stover, straw for example rice, wheat, rye, oat, barley, rape, bagasse, *miscanthus*, sorghum residue, grasses including coastal Bermuda grass and switch grass, bamboo, water hyacinth, wood consisting of hardwood e.g. *Salix* spp., *Eucalyptis* spp., hardwood chips, hardwood pulp, wood consisting of softwood e.g. *Pinus sylvestris, Pinus radiate*, softwood pulp and softwood chips.

The term "Pre-treatment" refers to a manipulation of lignocellulosic biomass that renders its cellulosic components more accessible to enzymes that convert carbohydrate polymers into fermentable sugars.

Pre-treatment of the lignocellulosic materials comprises one or more of the group consisting of removing or altering lignin, removing hemicellulose, decrystallizing cellulose, removing acetyl groups from hemicellulose, reducing the degree of polymerization of cellulose, increasing the pore volume of lignocellulose biomass, and increasing the surface area of lignocellulose. The pre-treatment may comprise one or more pretreatment technique selected from the group comprising autohydrolysis, steam explosion, grinding, chopping, ball milling, compression milling, radiation, flow-through liquid hot water treatment, dilute acid treatment, concentrated acid treatment, peracetic acid treatment, supercritical carbon dioxide treatment, alkali treatment, organic solvent treatment, cellulose solvent treatment and treatment with an aerobic fungi.

Preferably, the pre-treatment of a lignocellulosic biomass according to the invention can be realized with an acid treatment at a high temperature, e.g. at a temperature comprised between 110-250° C.

The term "fermenting microorganism" refers to any organism suitable for use in a desired fermentation process. Suitable fermenting microorganisms are according to the invention capable of fermenting, i.e. converting, carbohydrates directly or indirectly into a fermentation product, preferably ethanol.

Examples of fermenting microorganisms according to the invention include fungal organisms, such as yeast. Preferred yeast includes strains of the *Saccharomyces* spp., and in particular *Saccharomyces cerevisiae*. Commercially available yeast includes, e.g., RED STAR®/Lesaffre Ethanol Red (available from Red Star/Lesaffre, USA), SUPERSTART (available from Alltech), GERT STRAND (available from Gert Strand AB, Sweden) and FERMIOL (available from DSM Specialties). Further guidance in respect of using yeast for fermentation can be found in, e.g., "The alcohol Textbook" (Editors K. Jacques, T. P. Lyons and D. R. Kelsall, Nottingham University Press, United Kingdom 1999), which is hereby incorporated by reference.

Fermenting microorganisms according to the invention also include microorganisms capable of using pentose and gluconic acid through the pentose phosphate pathway. Indeed, several organisms use gluconic acid through the pentose phosphate pathway. *Zymomonas mobilis*, for example, is able to produce ethanol from gluconic acid by the Entner-Doudoroff pathway. Alcoholic fermentation from gluconic acid by *Saccharomyces bulderi* has also been reported. As the gluconic acid production is increased by using a composition according to the invention, as it has been demonstrated by the inventors, the introduction of such organisms able to use pentose and gluconic acid should increase the overall yield of ethanol by using less fermentable components and should offer a way to design a sustainable process for second generation bioethanol production.

DETAILED DESCRIPTION OF THE INVENTION

In a first aspect, the invention relates to a composition comprising at least:
  a) An enzyme cocktail of cellulases from *Trichoderma reesei*, and
  b) An enzyme cocktail from *Pycnoporus cinnabarinus* comprising a cellobiose dehydrogenase (CDH), or
  c) A recombinant cellobiose dehydrogenase from *Pycnoporus cinnabarinus*.

In a particular embodiment of the invention, the composition comprises b) an enzyme cocktail from *Phanerochaete chrysosporium* comprising a cellobiose dehydrogenase (CDH), or c) a recombinant cellobiose dehydrogenase from *Phanerochaete chrysosporium* instead of b) an enzyme cocktail from *Pycnoporus cinnabarinus* comprising a cellobiose dehydrogenase (CDH), or c) a recombinant cellobiose dehydrogenase from *Pycnoporus cinnabarinus* as disclosed previously.

In a preferred embodiment, the composition according to the invention can further comprise a β-glucosidase. Most preferably, the composition according to the invention further comprises a β-glucosidase from *Aspergillus niger*.

In another preferred embodiment, the composition according to the invention can further comprise an enzyme cocktail from *Aspergillus niger*, said enzyme cocktail comprising a β-glucosidase.

In a preferred embodiment, an enzyme cocktail of cellulases from *Trichoderma reesei* corresponds to the secretome of said *Trichoderma reesei*.

Methods for obtaining such cocktail are well known from the skilled person. Such cocktails are commercially available such as the GC220 (GENENCOR), the Multifect GC (GENENCOR) and the Celluclast 1.5L (NOVOZYME).

In another preferred embodiment, an enzyme cocktail from *Pycnoporus cinnabarinus* comprising a cellobiose dehydrogenase (CDH) corresponds to the secretome of said *Pycnoporus cinnabarinus*.

In a preferred embodiment, a recombinant cellobiose dehydrogenase according to the invention corresponds to a *Pycnoporus cinnabarius* cellobiose dehydrogenase.

In a still preferred embodiment, a recombinant cellobiose dehydrogenase according to the invention has a sequence selected in the group comprising the sequences SEQ ID No1 (CDH *Pycnoporus cinnabarinus*, accession number GenBank: AAC32197) and SEQ ID No2 (CDH *Pycnoporus cinnabarinus*, accession number GenBank: ADX41688).

In a still preferred embodiment, a recombinant cellobiose dehydrogenase according to the invention is produced in a recombinant microorganism such as for example *Pichia pastoris*.

In a still preferred embodiment, a composition according to the invention does not comprise a Family 61 glycoside hydrolase.

In another particular preferred embodiment, a composition according to the invention further comprises a Family 61 glycoside hydrolase. Indeed, the inventors have demonstrated that the supplementation of the composition according to the invention as disclosed previously with a Family 61 glycoside hydrolase led to a synergistic effected to a synergistic effect of the combination of CDH from *Pycnoporus cinnabarinus* and GH61.

In a still preferred embodiment, said Family 61 glycoside hydrolase is a Family 61 glycoside hydrolase from the ascomycete *Podospora anserina*.

In another still preferred embodiment, Family 61 glycoside hydrolase from the ascomycete *Podospora anserina* is selected among SEQ ID No12 and SEQ ID No13.

In another still preferred embodiment, Family 61 glycoside hydrolase from the ascomycete *Podospora anserina* is selected among SEQ ID No12, SEQ ID No13 and SEQ ID No14.

Another aspect of the invention concerns a method for degrading a lignocellulosic biomass, wherein said method comprises a step of treating said lignocellulosic biomass with a composition as defined previously.

In another aspect, the invention concerns the use of a composition as defined previously for the degradation of a lignocellulosic biomass.

A fermentation product production process of the invention generally involves the steps of liquefaction, saccharification, fermentation and optionally recovering the fermentation product.

Therefore, another aspect of the invention concerns a method for producing a fermentation product from a lignocellulosic biomass, said method comprising the following steps:
  a) Liquefaction of a lignocellulosic biomass by using a composition according to the invention as defined previously in order to obtain a liquefied product having a dry weight of at least 20%,
  b) Saccharification of the liquefaction product obtained from step a) with an enzyme cocktail,
  c) Fermentation of the saccharification product obtained from step b) by using a fermenting microorganism.

In a preferred embodiment, the fermentation product produced according to the method of the invention is an alcohol, an organic acid, a ketone, an amino acid, or a gas. Still preferably, the fermentation product according to the invention is bioethanol.

In a preferred embodiment, the liquefaction of lignocellulosic biomass preferably last up about 6 hours and is realized at a temperature not exceeding 90 Celsius degrees (° C.). Preferably, the liquefaction according to the invention is realized at a temperature comprised between 55° C. and 90° C., most preferably at a temperature of 65° C.

Indeed, at higher temperatures, viscosities are inherently lower and the reaction rates are higher, potentially reducing processing times and leading to lower investment and energy costs. The recombinant CDH produced by the inventors have been demonstrated to be thermostable and therefore suitable for being used in such method.

In a preferred embodiment, the dry weight of the liquefied product, i.e. the lignocellulosic biomass which has been liquefied in step a) according to the invention, is of at least 20%, preferably 25% and most preferably is comprised between 25-50%.

Indeed, in order to produce an ethanol fermentation product with a final concentration in the fermentation broth higher than 4% (w/w), which is considered as a prerequisite for feasible large scale distillation process, the dry weight has to be at least of 20% for lignocellulosic substrates.

In another preferred embodiment, a saccharification step of the invention may last up from 20 to 100 hours, preferably about 24 to about 72 hours, still preferably 48 hours, and may preferably be carried out at a temperature in the range from about 30 to 65° C., preferably at 55° C. or 65° C.

In still another preferred embodiment, an enzyme cocktail used for the saccharification step b) according to the method of the invention comprises at least two carbohydrolytic enzymes, said enzymes being capable of degrading cellulose and/or hemicellulose or parts thereof from lignocellulosic biomass into glucose, xylose, cellobiose, gluconic acid, xylonic acid and/or xylobionic acid, preferably glucose, xylose, cellobiose and gluconic acid. Such enzymes are added to the biomass either in native form or in form of microbial organisms giving rise to the accumulation of such enzymes. The pH and the temperature of the biomass are adjusted with reference to the pH-optimum and the temperature optimum of the enzymes applied.

In a still preferred embodiment, the enzyme cocktail used in the saccharification step b) corresponds to a composition according to the invention as disclosed previously.

In another embodiment, the liquefaction step a) and the saccharification step b) are carried out simultaneously as an enzymatic hydrolysis step.

From the lignocellulosic biomass prepared during liquefaction and saccharification stages, or during an enzymatic hydrolysis step, the fermentation leads to a fermented lignocellulosic biomass with high alcoholic content.

Fermentation is ongoing for 24-96 hours, such as typically 35-65 hours. In a preferred embodiment, the temperature in the fermentation step does not exceed 40° C., preferably said temperature is comprised between 26-40° C.

Saccharification and fermentation according to the method for the production of a fermentation product can be run in a Simultaneous Saccharification and Fermentation (SSF) step after liquefaction step a): enzymatic hydrolysis occurs at the same time as Fermentation. This scheme allows the maintaining of a low residual sugar content in the fermentors, favourable to the enzymatic kinetics and to yeasts development. Furthermore, the development of contaminants is limited.

The most widely used process in ethanol production is the simultaneous saccharification and fermentation (SSF) process, in which there is no holding stage for saccharification, meaning that the fermenting organism, such as yeast, and enzyme(s) is(are) added together. When the process is carried out as a simultaneous saccharification and fermentation process (SSF process) the temperature used in typically in the range from 30-40° C., preferably around 32° C.

Therefore, in another embodiment, the saccharification step b) and the fermentation step c) are carried out as a simultaneous saccharification and fermentation step (SSF) after liquefaction step a).

In a preferred embodiment, the single saccharification and fermentation step according to the invention preferably lasts up from 48 hours to 72 hours. In another preferred embodiment, said saccharification and fermentation step is realized at a temperature not exceeding 40° C.

In another embodiment, the method for producing a fermentation product from a lignocellulosic biomass according to the invention comprises a further step d) of recovering the fermentation product from step c).

Methods for recovering a fermentation product, such as bioethanol, are well known from one skilled in the art and include for example the distillation.

In another embodiment, the fermentation in step (c) and the recovering of the fermentation product in step (d) is carried out simultaneously; optionally followed by one or more process steps for further refinement of the fermentation product, such as bioethanol.

In a preferred embodiment, said method of producing a fermentation product comprises a further step of recovering the fermented biomass from step (c). Such a fermented biomass can be used for producing methane after ethanol recovery.

Another aspect of the invention relates to a fermentation product obtained from the method of producing a fermentation product as defined previously. In a preferred embodiment, said fermentation product is bioethanol.

Another aspect of the invention relates to the use of a composition according to the invention for the production of a fermentation product from a lignocellulosic biomass.

In a preferred embodiment, the fermentation product is bioethanol.

Another aspect of the invention concerns a method for producing gluconic acid, xylonic acid and/or xylobionic acid from a lignocellulosic biomass, wherein said method comprises the following steps:
a) Liquefaction of a lignocellulosic biomass by using a composition according to the invention as defined previously in order to obtain a liquefied product having a dry weight of at least 20%,
b) Saccharification of the liquefaction product obtained from step a) with an enzyme cocktail.

The steps a) and b) of liquefaction and saccharification are defined as disclosed previously in the method for producing a fermentation product hereabove.

In another embodiment, the liquefaction step a) and the saccharification step b) are carried out simultaneously as an enzymatic hydrolysis step.

In another embodiment, the method for producing gluconic acid, xylonic acid and/or xylobionic acid from a lignocellulosic biomass according to the invention comprises a further step c) of recovering the gluconic acid, xylonic acid and/or xylobionic acid from step b). Methods for recovering gluconic acid, xylonic acid and/or xylobionic acid are well known from one skilled in the art.

Another aspect of the invention relates to gluconic acid, xylonic acid and/or xylobionic acid obtained from the method of producing gluconic acid as defined previously.

Another aspect of the invention concerns the use of a composition as defined here above for the production of gluconic acid, xylonic acid and/or xylobionic acid from a lignocellulosic biomass.

Another aspect of the invention concerns a method for enhancing the production of gluconic acid, xylonic acid and/or xylobionic acid from a lignocellulosic biomass, wherein said method comprises the following steps:
 a) Liquefaction of a lignocellulosic biomass by using a composition according to the invention as defined previously in order to obtain a liquefied product having a dry weight of at least 20%,
 b) Saccharification of the liquefaction product obtained from step a) with an enzyme cocktail.

The steps a) and b) of liquefaction and saccharification are defined as disclosed previously in the method for producing a fermentation product hereabove.

In another embodiment, the liquefaction step a) and the saccharification step b) are carried out simultaneously as an enzymatic hydrolysis step.

The enhancement of the production of gluconic acid, xylonic acid and/or xylobionic acid according to the invention can be compared to the production of gluconic acid, xylonic acid and/or xylobionic acid from a same lignocellulosic biomass by using a composition comprising an enzyme cocktail of cellulases from *Trichoderma reesei*, preferably also comprising a β-glucosidase.

In a preferred embodiment, the production of gluconic acid, xylonic acid and/or xylobionic acid according to the invention is enhanced of at least 10%, preferably of at least 30%, most preferably of at least 50%.

In another embodiment, the method for enhancing the production of gluconic acid, xylonic acid and/or xylobionic acid from a lignocellulosic biomass according to the invention comprises a further step c) of recovering the gluconic acid, xylonic acid and/or xylobionic acid from step b). Methods for recovering gluconic acid, xylonic acid and/or xylobionic acid are well known from one skilled in the art.

Another aspect of the invention concerns the use of a composition as defined previously for enhancing the production of gluconic acid, xylonic acid and/or xylobionic acid from a lignocellulosic biomass compared to the production of sugars from a same lignocellulosic biomass by using a composition comprising an enzyme cocktail of cellulases from *Trichoderma reesei*, preferably also comprising a β-glucosidase.

Another aspect of the invention concerns a method for enhancing the production of sugars from a lignocellulosic biomass, wherein said method comprises the following steps:
 a) Liquefaction of a lignocellulosic biomass by using a composition according to the invention as defined previously in order to obtain a liquefied product having a dry weight of at least 20%,
 b) Saccharification of the liquefaction product obtained from step a) with an enzyme cocktail.

The steps a) and b) of liquefaction and saccharification are defined as disclosed previously in the method for producing a fermentation product hereabove.

In another embodiment, the liquefaction step a) and the saccharification step b) are carried out simultaneously as an enzymatic hydrolysis step.

The enhancement of the production of sugars according to the invention can be compared to the production of sugars from a same lignocellulosic biomass by using a composition comprising an enzyme cocktail of cellulases from *Trichoderma reesei*, preferably also comprising a β-glucosidase.

In a preferred embodiment, sugars whose production is enhanced according to the method of the invention comprise galactose, xylose and/or arabinose.

In a preferred embodiment, the production of sugars according to the invention is enhanced of at least 5%, preferably of at least 10%, 20% 30%, most preferably of at least 50%.

In another embodiment, the method for enhancing the production of sugars from a lignocellulosic biomass according to the invention comprises a further step c) of recovering the sugars from step b). Methods for recovering sugars are well known from one skilled in the art.

Another aspect of the invention concerns the use of a composition as defined previously for enhancing the production of sugars from a lignocellulosic biomass compared to the production of sugars from a same lignocellulosic biomass by using a composition comprising an enzyme cocktail of cellulases from *Trichoderma reesei*, preferably also comprising a β-glucosidase.

In another embodiment, the methods for degrading a lignocellulosic biomass, for producing a fermentation product, for producing gluconic acid, xylonic acid and/or xylobionic acid, for enhancing the production of gluconic acid, xylonic acid and/or xylobionic acid and for enhancing the production of sugars from a lignocellulosic biomass according to the invention and as disclosed previously may comprise a former step of milling the lignocellulosic biomass before the liquefaction step a).

In another embodiment, the methods for degrading a lignocellulosic biomass, for producing a fermentation product, for producing gluconic acid, xylonic acid and/or xylobionic acid, for enhancing the production of gluconic acid, xylonic acid and/or xylobionic acid and for enhancing the production of sugars from a lignocellulosic biomass according to the invention and as defined previously, may comprise a former step of pre-treatment of the lignocellulosic biomass before the liquefaction step a), said pre-treatment enabling to increase enzymatic digestibility.

In a still preferred embodiment, the step of pre-treatment of the lignocellulosic biomass can be realized according to the methods which are defined previously, preferably an acid an acid treatment at a high temperature, e.g. at a temperature comprised between 110-250° C.

In a still preferred embodiment, a lignocellulosic biomass used according to the invention may have been previously pre-treated. Still preferably, the lignocellulosic biomass used according to the invention may have been previously pre-treated with an acid treatment at a high temperature, e.g. at a temperature comprised between 110-250° C.

Another aspect of the invention concerns the use of a recombinant cellobiose dehydrogenase from *Pycnoporus cinnabarinus* as defined previously under high temperatures. In a preferred embodiment, high temperatures according to the invention are comprised between 55-90° C.

EXAMPLES

Example 1

Production of a Recombinant *P. cinnabarinus* CDH and Tests of Lignocellulosic Degradation with Compositions Comprising an Enzyme Cocktail of Cellulases from *T. reesei* and CDH from *P. cinnabarinus*

Biological Material
*P. cinnabarinus* ss3 monokaryotic strain BRFM 137 isolated from the fruit-like structure of the *P. cinnabarinus* I-937 dikaryotic strain was maintained as previously described (Herpoel, I., et al, 2000, FEMS Microbiology Letters, vol. 183, pp: 301-306). *P. pastoris* strain X33 is a component of the *Pichia* Easy Select Expression System and the pPICZαA vector (INVITROGEN, Cergy-Pontoise, France).

Media and Culture Conditions

*P. cinnabarinus* was grown at 30° C. on MYA2 plates (maltose: 20 g·l$^{-1}$; yeast extract: 1 g·l$^{-1}$; agar 16 g·l$^{-1}$). After 10 days of incubation, precultures in Roux flasks containing 200 ml of medium according to Sigoillot et al. (1996, Applied and Environemental Microbiology, vol. 62, pp: 1329-1335) were inoculated by five disks of *P. cinnabarinus* grown in MYA2 plates. Inoculum was obtained from 10-day-old static precultures incubated at 30° C.

We used 10 ml of inoculum suspension obtained from Ultra-Turrax-mixed mycelial mats to inoculate 500 ml baffled conical flasks containing 250 ml of basal medium composed of: cellulose fibrous medium (SIGMA, St. Louis, Mo., USA) or cellulose CC41 (WHATMAN, Versailles, France) (15 g·l$^{-1}$); diammonium tartrate (1.84 g·l$^{-1}$); disodium tartrate (2.3 g·l$^{-1}$); $KH_2PO_4$ (1.33 g·l$^{-1}$); $CaCl_2.H_2O$ (0.1 g·l$^{-1}$); $MgSO_4.7H_2O$ (0.5 g·l$^{-1}$); $FeSO_4.7H_2O$ (0.07 g·l$^{-1}$); $ZnSO_4.7H_2O$ (0.046 g·l$^{-1}$); $MnSO_4.H_2O$ (0.035 g·l$^{-1}$); $CuSO_4.5H_2O$ (0.007 g·l$^{-1}$); yeast extract (1 g·l$^{-1}$); vitamin solution according to Tatum et al. (1950, American Journal of Botany, vol. 37, pp: 38-46); (1 ml·l$^{-1}$); maltose (2.5 g·l$^{-1}$) used as starter and Tween 80 (1.5 g·l$^{-1}$) according to (Sigoillot, C., A. et al, 2002, Enzyme and Microbial Technology, Vol. 31, pp: 876-883). For the heterologous expression of CDH in *Pichia*, all media and protocols are described in the *Pichia* expression manual (INVITROGEN). Cloning procedures were performed using one-shot TOP 10 and DH5α chemically competent *Escherichia coli* cells (INVITROGEN).

Isolation of mRNA and Cloning of cdh cDNA Gene

Isolation of total RNA was performed on a 4-day-old culture of *P. cinnabarinus* on cellulose medium using Total RNA Purification from Plant (MACHEREY-NAGEL, Düen, Germany) as prescribed by the manufacturer. Contaminant DNA was digested by Turbo DNase (AMBION INC., Austin, Tex., USA) according to the manufacturer's instructions. First-strand cDNA synthesis was performed using SuperScript reverse transcriptase (INVITROGEN) and oligo (dT$_{18}$) primer following the manufacturer's instructions. The amplification of the full-length cdh cDNA was performed using specific primers (with restriction sites underlined): forward primer cdhF of SEQ ID No3 (5' TA GAATCC CAA GTG GCA GCG CCA TAC 3') and the reverse primer cdhR of SEQ ID No4 (5' TA TCTAGA CCA GGA CCT CCC GCA AGG GC 3') designed from *P. cinnabarinus* I-937 cdh gene (NCBI AF081574): 315 ng of cDNA was mixed with 300 pmol of each primer cdhF and cdhR, 200 μM dNTPs, and 0.5 U Pfu DNA polymerase (PROMEGA, Madison, Wis., USA). The reaction was performed following the amplification program: 1 cycle at 95° C. for 5 min, 30 cycles composed of three steps for each cycle (95° C. for 1 min; 65° C. for 30 s and 72° C. for 4 min), and a final step of 72° C. for 10 min. PCR amplicons generated by Pfu DNA polymerase are blunt-ended. To add an A-tail on these PCR fragments before subcloning into pGEMT-easy vector, Taq DNA polymerase (PROMEGA) was used as described in pGEMT-easy vector Technical Manual (PROMEGA). The 2.3 kb PCR product was purified using the Qiaquick gel extraction kit (QIAGEN, Valencia, Calif., USA) and subcloned into pGEMT easy vector.

The cdh cDNA was further sequenced (GATC BIOTECH, Mulhouse, France) using sp6 and T7 universal primers and cdhint of SEQ ID No5 (5' CGA CGC CCA GAA CTC GAA C 3'). The *P. cinnabarinus* sequence was deposited in the NCBI databank (GenBank accession number: HQ825322). Comparisons of *P. cinnabarinus* I 937 cdh (GenBank accession number: AF081574.1), *T. versicolor* cdh (GenBank accession number: AY187939.1) and *P. chrysosporium* cdh (GenBank accession number: U46081.1) were performed with ClustalW2 software (http://www.ebi.ac.uk/Tools/msa/clustalw2/).

Construction of pPiCZαA Expression Vector

The cdh cDNA cloned into pGEMT easy vector was digested using EcoRI and XbaI and purified with a QIAQUICK gel extraction kit. In parallel, pPICZαA was linearized using the same restriction enzymes, and cdh cDNA was ligated at the corresponding sites into pPICZαA in frame with both the yeast α-secretion factor and C-term-(His)$_6$-tag encoding sequences. Expression vector pPICZαA-cdh was purified by QIAGEN MIDIPREP and sequenced using 3'AOX and 5'AOX primers to confirm the correct sequence insertion.

Transformation and Screening

Transformation of competent *P. pastoris* X33 was performed by electroporation with PmeI linearized pPICZα A-cdh as described in Couturier et al. (2010, Applied and Environmental Microbiology, doi:10.1128/AEM.01761-10). The vector pPICZα without insert was used as a control. Transformants were first screened on YPDS plates with different concentrations of zeocin (100 to 1000 μg·ml$^{-1}$). After incubation at 30° C., transformants were picked from minimal dextrose (MD) plates and transferred to minimal methanol plates (MM). Zeocin-resistant *P. pastoris* transformants were then screened for protein expression in 10 ml of BMGY (in 50 ml tubes) at 30° C. in an orbital shaker (200 rpm) for 16 h to an OD$_{600}$ of 2-6, and expression was induced by transferring cells into 2 ml of BMMY and grown for another 3 days. Each day the medium was supplemented with 3% (v/v) methanol. The supernatant was then analyzed by SDS-PAGE to determine the transformant with the best secretion yield.

Recombinant CDH Production

The best-producing transformant was grown in 1 liter of BMGY in shaken flasks as described above. The cells were then transferred to 200 ml of BMMY and stirred at 200 rpm and 30° C. for 4 days.

Bioreactor production of the best-producing transformant was carried out in a 1-liter bioreactor according to the *Pichia* Fermentation Process Guidelines (INVITROGEN) except for the volume of methanol added in the methanol fed batch, which was changed from 3.6 ml·h$^{10}$·l$^{-1}$ to 3 ml·h$^{10}$·l$^{-1}$.

Enzyme Purification

Culture supernatant was concentrated at least 10 times using Amicon centrifugal units with a 30 kDa cut-off, 4000×g or Amicon vivaflow (MILLIPORE, Bedford, Mass., USA) with a 30 kDa cut-off depending on culture volume. The concentrated supernatant was dialyzed against buffer A (Tris-HCl 50 mM 7.8, NaCl 150 mM, imidazole 10 mM) and loaded on a nickel chelate His-Bind Resin (GE Healthcare, Buc, France) column (0.7×5 cm) connected to an Äkta FPLC (GE Healthcare) and equilibrated with buffer A. The His-tagged rCDH was eluted with buffer B (Tris-HCl 50 mM pH 7.7, imidazole 500 mM, NaCl 150 mM). Active fractions were pooled, concentrated and dialyzed against sodium acetate buffer (50 mM, pH 5)

SDS-PAGE, Western Blot and Zymogram

Polyacrylamide gel electrophoresis (SDS-PAGE) (12%) was prepared as described by Laemmli (1970, Nature, vol. 227, pp: 680-5). Protein bands were stained with Coomassie blue G 250. The molecular mass under denaturating conditions was determined with reference standard proteins (LMW, AMERSHAM PHARMACIA BIOTECH, Orsay, France).

Enzyme activities were assayed in polyacrylamide gels containing the appropriate substrates. Enzyme preparations were run on an SDS-PAGE gel copolymerized with 0.2% soluble xylan, 0.2% carboxymethylcellulose (CMC) or 0.2% locust bean gum for the analysis of xylanase, CMCase or mannanase activities, respectively. The protein samples were mixed in the loading buffer (3% SDS w/v; 10% glycerol w/v; 30 mM Tris-HCl buffer pH 6.8) without reducing agent and heated at 100° C. for 1 mM before separating using a 12% polyacrylamide gel. After electrophoresis, the gel was washed with de-ionized water and soaked in 2.5% (v/v) Triton X-100. After 1 h incubation at 4° C., the gel was soaked in 100 mM sodium phosphate buffer (pH 5) at 45° C. for 2 h for the detection of xylanase and CMCase activity or in 100 mM sodium phosphate buffer (pH 7) for 1 h at 50° C. for the detection of mannanase activity. After incubation the gel was stained with 0.1% Congo red solution under gentle shaking for 1 h and destained with 1M NaCl for 1 h. Protein bands exhibiting xylanase, CMCase and mannanase activity were observed as clear bands on the red background.

For laccase and CDH zymograms, samples were mixed with the same loading buffer as described above without heating; they were incubated at ambient temperature for 15 min before running the gel. After electrophoresis, the gel was soaked in 2.5% Triton X-100 for 1 h at 4° C., rinsed with deionized water and incubated for 2 h at 25° C. in 50 mM sodium acetate buffer (pH 5) with 4 mM sodium fluoride for CDH and 50 mM sodium tartrate buffer (pH 4) for laccase. Visualization was performed with addition of 5 mM ABTS until staining for laccase and addition of 50 mM DCPIP for CDH, staining the gel dark blue. CDH activity was then visualized by adding 100 mM cellobiose. Protein bands exhibiting CDH activity were observed as clear bands on the dark blue background. Western blot analysis was performed as described previously, using the monoclonal anti-polyhistidine alkaline phosphatase conjugate (SIGMA) for Western blot analysis of rCDH expressed in $P.$ $pastoris$. For Western blot analysis, purified rCDH was run on a 12% SDS/polyacrylamide gel and blotted onto a PVDF membrane using the iBlot Dry Blotting System (INVITROGEN). Membranes were placed in a Snap Protein Detection System (MILLIPORE, Bedford, Mass., USA) used for immunodetection. Following the manufacturer's instructions, the PVDF membrane was incubated in TBS blocking solution (10 mM Tris, 150 mM NaCl, 0.1% Tween 20, pH 8) with addition of 0.1% (w/v) of skimmed milk powder and then washed with TBS. Immunodetection was performed using the monoclonal anti-polyhistidine alkaline phosphatase conjugate (SIGMA). Signal detection was carried out using 60 µl of BCIP (5-bromo-4-chloro-3-indolyl-phosphate), 60 µl of NBT (4-nitro blue tetrazolium) (ROCHE APPLIED SCIENCE, Meylan, France) in 20 ml carbonate buffer 0.05M pH 9.6 with addition of 5 mM $MgCl_2$.

Papain cleavage of the two CDH modules was carried out as described by Henriks son et al (1991, European Journal of Biochemistry, Vol. 196, pp: 101-106). Deglycosylation was performed using PGNase (NEW ENGLAND BIOLABS, Saint-Quentin-en-Yvelines, France) to remove rCDH N-linked glycans according to the manufacturer's instructions.

Protein Determination

Protein concentration was determined using the Bio-Rad Protein Assay (BIO-RAD, Marnes-la-Coquette, France), based on the Bradford procedure, using bovine serum albumin as standard (Bradford, M. M., 1976, Analytical Biochemistry, vol. 72, pp: 248-254).

Binding Studies

Three types of celluloses (Avicel PH-101, cellulose medium fibrous (SIGMA) and cellulose CC41 (WHATMAN)) were selected for binding assays. Assays were performed with 1 mg·ml$^{-1}$ of cellulose in 50 mM citrate phosphate buffer pH 5 under orbital agitation at room temperature, and rCDH was added at a concentration of 8 µM. After 3 h, samples were centrifuged for 5 min at 14,000 rpm, and the supernatants were collected for activity assays. To determine binding parameters ($B_{max}$ and $K_d$), Avicel PH-101 was chosen for best cellulose fixation. Conditions were the same except for rCDH concentration, which ranged between 0.2 and 8 µM. Two controls were performed, one without rCDH and the other with BSA at 1 µg·µl$^{-1}$ to estimate unspecific fixation of rCDH.

Enzyme Assays

To measure enzyme activities in the $P.$ $cinnabarinus$ culture supernatant, each aliquot was centrifuged for 5 min at 3500 rpm and filtered through a 0.45 µm membrane (MILLIPORE, Bedford, Mass., USA). CDH activities were determined by monitoring the reduction of 0.2 mM 2,6-dichlorophenol indophenol (DCPIP) in 100 mM sodium acetate buffer (pH 5) containing 2 mM cellobiose and 4 mM of sodium fluoride (sodium fluoride was used as a laccase inhibitor). The decrease in absorption at 520 nm ($\epsilon$=6800 $M^{-1} \cdot cm^{-1}$) was monitored at 30° C. for 1 min. Alternatively, CDH activity was determined by monitoring the reduction of 50 µM cytochrome c (cyt c) in 100 mM sodium-acetate buffer (pH 5) containing 2 mM cellobiose. The decrease in absorption at 550 nm ($\epsilon$=33,700 $M^{-1} \cdot cm^{-1}$) was monitored at 30° C. for 1 min. Glucose oxidase was measured by using the D-gluconic acid/D-glucono-δ-lactone assay (MEGAZYME). Laccase activity was determined quantitatively by monitoring the oxidation of 5 mM ABTS (2,2'-azino-bis(3-ethylbenzthiazoline-6-sulfonic acid)) at 420 nm (extinction coefficient 36,000 mM.$^{-1}$ cm.$^{-1}$) in the presence of 50 mM NaK tartrate, pH 4.0. Lignin peroxidase activity was determined spectrophotometrically at 30° C. by the method of Tien and Kirk (1988, Methods Enzymol., vol. 161, pp: 238-249). Manganese peroxidase activity was determined spectrophotometrically at 30° C. by the method of Paszczynski et al. (1985, FEMS Microbiol. Lett. 29:37-41) using $H_2O_2$ and vanillylacetone as substrate. Enzyme activity was expressed in international units (IU). One unit of activity is defined as the quantity of enzyme that transforms 1 µmol of substrate in one minute.

Hydrolysis assays for glycosidases were carried out in 50 mM acetate buffer pH 5 containing 1 mM of substrate in a final volume of 100 µl. Substrates pNP-β-D-glucopyranoside, pNP-β-D-cellobiopyranoside, pNP-β-D-xylopyranoside, α-D-galactopyranoside and pNP-β-D-mannopyranoside were purchased from Sigma. Assays were performed with 0.5 and 1 µg of protein, incubated for 37° C. for 1 h with shaking (300 rpm). To stop the reaction, 130 µl of $Na_2CO_3$ 1M was added, and absorbance was read at 410 nm. A control was run with 100 µL of 50 mM acetate buffer pH 5 and references ranging from 0.02 to 0.2 mM of 4-nitrophenyl were measured in parallel. Enzymatic activity was based on colorimetric assay of free pNP present in the reaction after hydrolysis. This activity is expressed in U·mg$^{-1}$ of proteins.

Hydrolysis assays were carried out in 50 mM acetate buffer pH 5 containing 1% (w/v) of substrates. Carboxymethyl cellulose (CMC, low viscosity) and citrus pectin were purchased from Sigma. Wheat arabinoxylan (low viscosity) and galactomannan (low viscosity) were from MEGAZYME. Assays were performed with 10 and 30 μg of protein, incubated at 37° C. for 1 h with shaking (150 rpm). Reducing sugars released during hydrolysis were quantified by DNS (3,5-dinitrosalycilic acid) visualization at 540 nm Controls were run with 50 mM acetate buffer pH 5 and references ranging from 1 to 10 mM of glucose were measured in parallel for each series. Enzymatic activity is expressed in U·mg$^{-1}$ of proteins. Three controls were performed with secretome alone to quantify sugars present in culture supernatant. Controls were subtracted from measured values. All assays were performed in triplicate.

Effect of pH and Temperature on the Activity and Stability of rCDH

To determine the optimum pH of the rCDH, the activity was measured with DCPIP using 50 mM citrate phosphate buffer in the pH range 2.5-7 at 30° C. For optimum temperature determination, activity on DCPIP was measured using 50 mM citrate phosphate buffer in the temperature range 10-80° C. Thermal stability of rCDH was determined by incubating enzymes for 33 h at 45, 50 and 55° C. and for 10 h at 65° C. Native CDH activity assay was performed in triplicate as described above.

Enzyme Kinetics

The kinetic parameters ($V_{max}$ and $K_m$) were determined for cellobiose oxidation measured at 30° C. in 50 mM citrate phosphate buffer pH 4.5 using DCPIP or cytochrome c. The concentration of cellobiose ranged from 10 to 700 μM with both electron acceptors (DCPIP and cytochrome c). Triplicates were run to ensure reliable kinetic parameter determination.

Graphpad prism v.4 (Graphpad Software) was used for the nonlinear regression calculation and kinetic parameter determination.

Saccharification Assays

Saccharification assays were performed in 50 ml Falcon tubes (BD BIOSCIENCE) containing 5% (w/v) wheat straw in 50 mM sodium phosphate buffer (pH 4.8) with addition of tetracycline (12.6 mg·ml$^{-1}$) and cycloheximide (10 mg·ml$^{-1}$). The final reaction volume was 20 ml. Enzymes were added to the basal medium: industrial cocktail GC220 (GENENCOR-DANISCO, Rochester, N.Y., USA) from *T. reesei* and Novozyme 188 (NOVOZYME, Franklinton, N.C., USA) from *Aspergillus niger*, *P. cinnabarinus* supernatants containing CDH activity and purified rCDH expressed by *P. pastoris*.

*T. reesei* GC220 enzyme cocktail contained 1.41 U CMCase, 0.79 U β-glucosidase, 0.11 U cellobiohydrolase, 3.85 U xylanase, 0.26 U mannanase and 0.14 U pectinase per mg of total protein. *A. niger* Novozyme 188 enzyme cocktail contained 0.06 cellobiohydrolase, 0.18 U CMCase, 1.15 U β-glucosidase, 0.33 U xylanase, 0.20 U mannanase, 0.14 U α-galactosidase and 0.43 U pectinase per mg of total protein. Activities were measured at 37° C., pH 5.0. Saccharification assays were performed in incubators (INFORS AG, Switzerland) at 45° C. with an orbital shaker (140 rpm) for 96 h. After 96 h of incubation, all the samples were centrifuged at 3500 rpm for 15 min. The supernatants were filtered through a 0.45 μm membrane before carbohydrate determination. Saccharification assays were performed in triplicate.

Carbohydrate Determination

Monosaccharides, cellobiose and gluconic acid generated after hydrolysis of wheat straw were quantified by high-performance anion exchange chromatography (HPAEC) coupled with amperometric detection (PAD) (ICS 3000, Dionex, Sunnyvale, Calif., USA) equipped with a Carbo-Pac PA-1 analytical column (250×4 mm) Enzymatic reactions were stopped by adding 18 mM NaOH before injection (5 μl) into the HPAEC system. Elution (1 ml·min$^{-1}$) was carried out on a sodium acetate gradient (0 to 250 mM in 25 min) Calibration curves were plotted using galactose, arabinose, glucose, xylose, cellobiose and gluconic acid standards (Sigma-Aldrich), from which response factors were calculated (CHROMELEON PROGRAM, DIONEX) and used to estimate the amount of product released in test incubations. All the assays were carried out in triplicate.

Results

Production and Characterization of *P. cinnabarinus* ss3 Secretome in Cellulolytic Conditions CDH is produced by *P. cinnabarinus* when cellulose is added to the culture medium. The best production (355 U·l$^{-1}$) appeared after 10 days of cultivation when cellulose is used as sole carbon source. The production is highly dependent on the type of cellulose used. Highest CDH activities were obtained with cellulose CC41 and cellulose fibrous medium (FIG. 1). However, no significant CDH activity was detected when Avicel was used as inducer (data not shown). To understand the role of CDH when secreted in cellulolytic conditions, we characterized the *P. cinnabarinus* secretome after 11 days of growth.

Main enzymatic activities present in *P. cinnabarinus* secretome in cellulolytic conditions were measured by assay on a range of substrates (Table 1). No significant laccase or peroxidase activities were detected under our experimental conditions. However, *P. cinnabarinus* secretome contained enzymes able to hydrolyze a broad range of polysaccharides. Significant levels of activities towards pNP-glucose, CMC and pNP-cellobiose were detected, corresponding to β-glucosidase (0.35 U·mg$^{-1}$), endoglucanase (0.55 U·mg$^{-1}$) and cellobiohydrolase (0.32 U·mg$^{-1}$). A variety of hemicellulases were also identified in *P. cinnbarinus* secretome. The two main endo-glycosidase activities were present corresponding to endo-mannanase and endo-xylanase with about 2 U·mg$^{-1}$. Hemicellulase exoglycosidase enzymes were detected to a lesser extent: 0.85 U·mg$^{-1}$ of α-galactosidase and 0.01 U·mg$^{-1}$ of 3-xylosidase were measured.

TABLE 1

Lignocellulose-degrading enzyme activities measured in *P. cinnabarinus* secretome. Results are expressed in U · mg$^{-1}$ of total proteins.

| Type of activity | Substrate | Activity (U · mg$^{-1}$) |
|---|---|---|
| CDH | Cellobiose | 0.53 |
| Laccase | ABTS | nd$^a$ |
| Glucose oxidase | Glucose | nd$^a$ |
| Manganese peroxidase | Vanillyl acetone | nd$^a$ |
| Lignin peroxidase | Veratryl alcohol | nd$^a$ |
| β-Glucosidase | pNP-glucose | 0.35 ± 0.00 |
| Endoglucanase | CMC | 0.55 ± 0.00 |
| Cellobiohydrolase | pNP-Cellobiose | 0.32 ± 0.00 |
| β-Xylosidase | pNP-Xylose | 0.01 ± 0.00 |
| Endo-xylanase | Low viscosity arabinoxylan | 2.03 ± 0.08 |
| β-Mannosidase | pNP-Mannose | nd$^a$ |
| Endo-mannanase | Galactomannan | 2.03 ± 0.11 |
| Pectinase | Pectin | 0.45 ± 0.02 |
| α-Galactosidase | pNP-Galactose | 0.85 ± 0.00 |

$^a$no activity detected

Zymogram assays were performed on the culture extract of *P. cinnabarinus* to give insight into the number of isoforms present for the main enzymatic activities previously measured.

Figure 2:
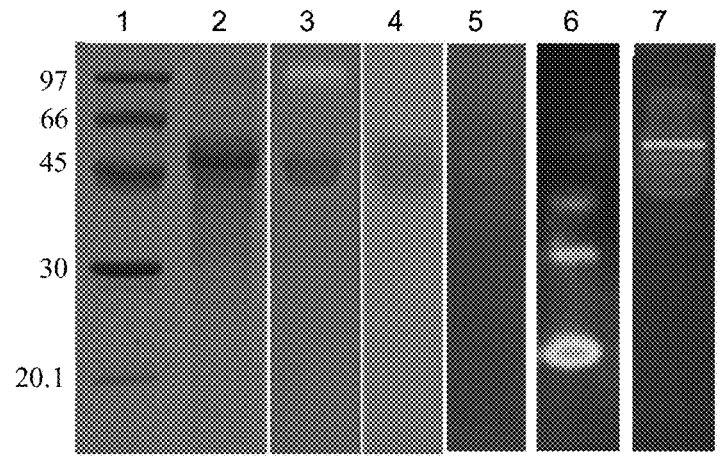
FIG. 2. SDS-PAGE and zymogram on the supernatant of *P. cinnabarinus* ss3 grown in cellulolytic condition. 1, pre-stained molecular weight marker; 2, SDS-PAGE with 10 µg of protein supernatant after ultrafiltration step; 3, CDH zymogram; 4, zymogram with ABTS; 5, soluble xylan birchwood (xylanase) zymogram; 6, CMC (endoglucanase) zymogram and 7, locust bean gum (mannanase) zymogram.

SDS-PAGE of *P. cinnabarinus* (FIG. 2, lane 2) grown in cellulolytic conditions presented two main differences when compared with reference culture supernatant grown in non-cellulolytic conditions: (i) the presence of a band around 100 kDa, attributable to CDH and (ii) the absence of 70 kDa band corresponding to laccase. Confirmation by the zymogram technique showed the DCPIP decoloration by the 100 kDa band corresponding to CDH activity (FIG. 2, lane 3). Oxidation of ABTS occurred at around 50 kDa (FIG. 2, lane 4) and could not be attributed to laccase which possesses a molecular mass of 70 kDa. The xylanase zymogram (FIG. 2, lane 5) demonstrated the presence of a weak activity at 50 kDa corresponding to the results previously described (Sigoillot, C., A. et al, 2002, as disclosed previously). CMCase zymogram (FIG. 2, lane 6) showed at least five bands with the brightest one at 25 kDa. For mannanase activity (FIG. 2, lane 7), some bands were represented around one major band at 60 kDa.

*P. cinnabarinus* CDH Sequence Analysis

Based on *P. cinnabarinus* ss3 cdh sequence, primers were designed to clone the cdh gene starting from 4-day-old culture induced with cellulose. The cdh sequence of 2310 bp was compared with available cdh sequences. Nucleotide sequence analysis showed 97% identity between cdh of *P. cinnabarinus* I 937 described by Moukha et al. (as disclosed previously) and the cdh from *P. cinnabarinus* ss3. *P. cinnabarinus* ss3 is a monokaryotic strain isolated from the fruit-like structure of *P. cinnabarinus* I 937, a wild-type dikaryotic strain. These observed differences in the nucleotide sequence resulted in 8 amino acid differences at positions 96 (Ala→Glu), 331 (Arg→Ser), 354 (Ala→Thr), 357 (Asn→Lys), 386 (Tyr→Ser), 426 (Tyr→Phe) and 495 (Gln→Glu). Comparison with *T. versicolor* cdh and *P. chrysosporium* cdh resulted in amino acid sequence identities of 77% and 70%, respectively. *P. cinnabarinus* cdh amino acid sequence exhibited conserved regions with GMC oxidoreductase (Zamocky, M., M. et al, 2004, Gene 338:1-14) conserved domain. The linker region rich in Thr-Ser (from position 182 to position 215), the FAD binding site and the Met/His ligands for heme fixation were also identified. It is interesting to note that the Thr-Ser region was also rich in Pro (28% Thr, 25% Pro, 13% Ser)

Heterologous Expression of CDH in *P. pastoris*

The coding sequence of cdh was inserted into the *P. pastoris* expression vector in frame with sequences encoding the yeast α-factor secretion peptide and a $(His)_6$ tag located at the C-terminus. The recombinant gene was then introduced into the *Pichia* genome under the control of the methanol-inducible promoter. Multi-copy transformants were screened to select a clone that exhibited satisfactory levels of production. CDH activity was successfully detected in the supernatant after induction, indicating correct processing of the α-factor signal sequence.

A maximum activity of 1176 U·l$^{-1}$ observed after 4 days of induction and this clone was chosen for this study. To scale up enzyme production, we optimized CDH expression in a 1-liter bioreactor with the best performing clone of *P. pastoris*. The recombinant CDH was secreted at high levels, reaching 7800 U·l$^1$. Recombinant CDH was purified after 4 days of induction, taking advantage of the $(His)_6$ tag. Also, only trace amounts of endogenous proteins were present in the culture supernatant of the transformant secreting CDH. The purified enzyme exhibited a specific activity of 22.2 U·mg$^{-1}$.

Biochemical Characterization of rCDH

Recombinant CDH was purified to homogeneity, i.e. one major band displaying a relative molecular weight around 110 kDa (FIG. 3, lane 2) was observed on SDS-PAGE. Western blot analysis (FIG. 3, lane 4) confirmed the presence of CDH at 110 kDa.

Figure 3:
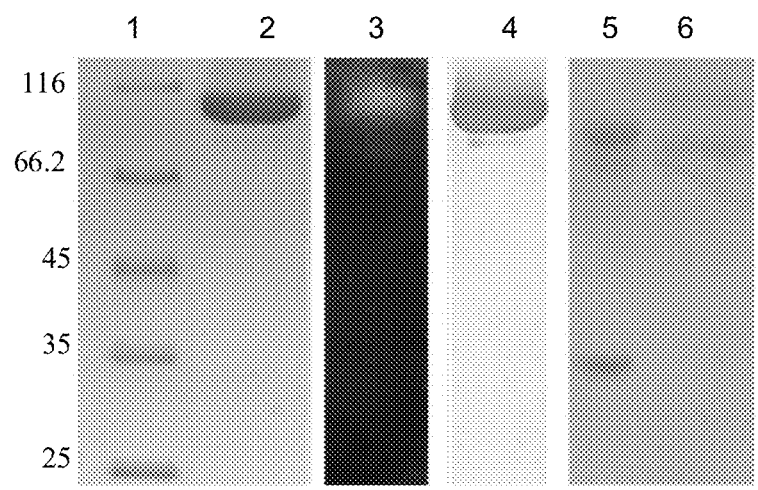
FIG. 3. SDS-PAGE, zymogram, immunoblot analysis, deglycosylation and cleavage by papain of purified recombinant rCDH. 1, pre-stained molecular weight marker; 2, 10 µg of purified CDH; 3, CDH zymogram on the sample 2; 4, Western blot analysis using anti-His antibodies; 5, CDH deglycosylated; 6, CDH digested by papain.

Zymogram analysis of CDH activity revealed active bands on the gel corresponding to 70 and 110 kDa. Deglycosylation (FIG. 3, lane 5) of CDH showed enhancement of degradation between the two enzyme moieties and a loss of approximately 10 kDa. Following papain cleavage of CDH, a band corresponding to the FAD-containing moieties was observed on SDS-PAGE (FIG. 3). The heme-containing moiety was not seen after staining, probably owing to the weak presence of aromatic residues (Henriksson, G., 1991, Eur. J. Biochem. 196:101-106).

Figure 4:
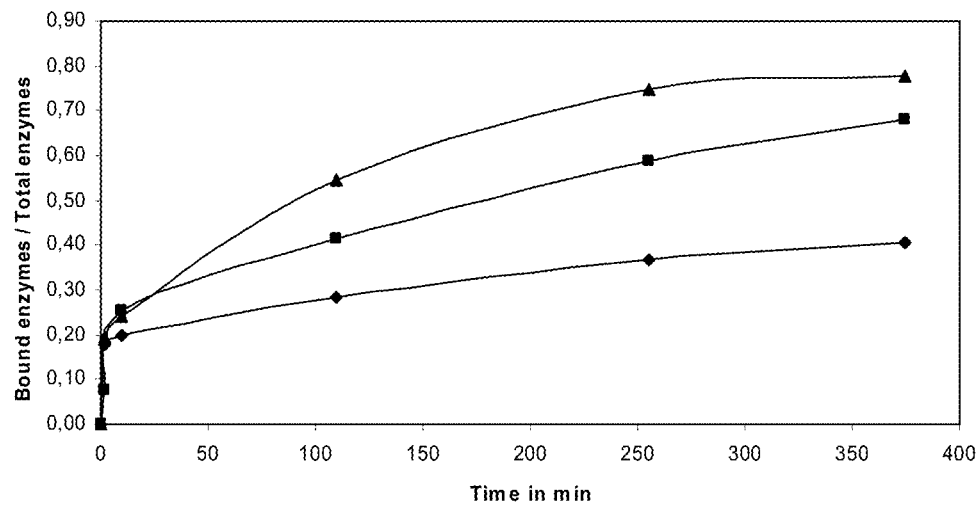
FIG. 4. Cellulose binding isotherm of rCDH (A) and kinetics of the binding of rCDH (B). Experiments were performed on Avicel at 30° C., pH 4.5.
Figure 4:
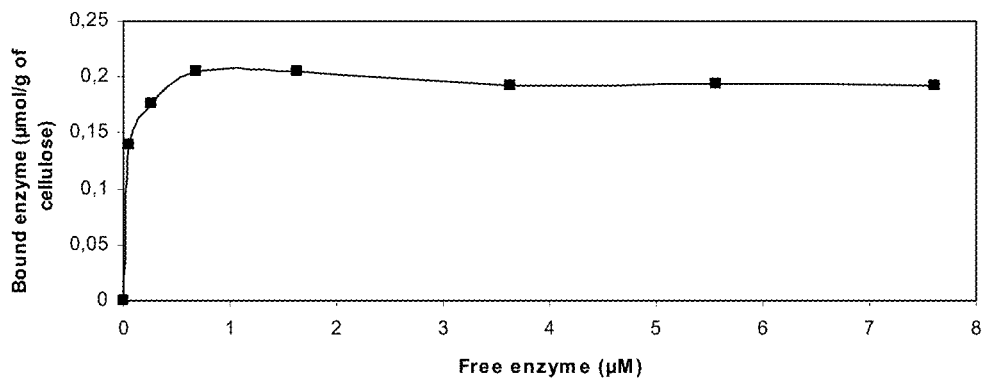

Binding studies of CDH confirmed the ability of the enzyme to bind cellulose without the presence of a cellulose-binding domain. The binding isotherm for different types of cellulose showed best binding of CDH for Avicel compared with others (FIGS. 4, A and B). Dissociation constant ($K_d$) and binding capacities ($B_{max}$) of CDH were determined and were respectively 0.064 μM and 20 mg·g$^{-1}$ of Avicel.

Figure 5:
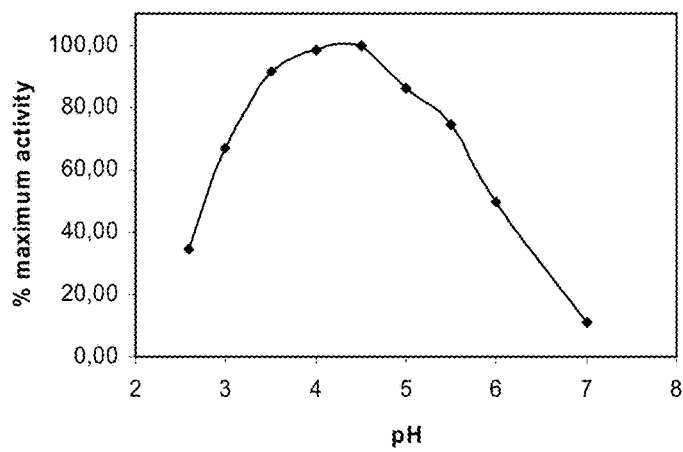
FIG. 5. Effect of temperature on the activity of purified rCDH using DCPIP as electron acceptor. Activity was determined at pH 4.5. (A) Temperature optimum. (B) Temperature stability at 45° C. (■), 50° C. (♦), 55° C. (▲) and 65° C. (□). (C) Optimal pH of purified rCDH using DCPIP as electron acceptor. Activity was determined at 30° C. in citrate-phosphate buffer pH 2.7-7.
Figure 5:
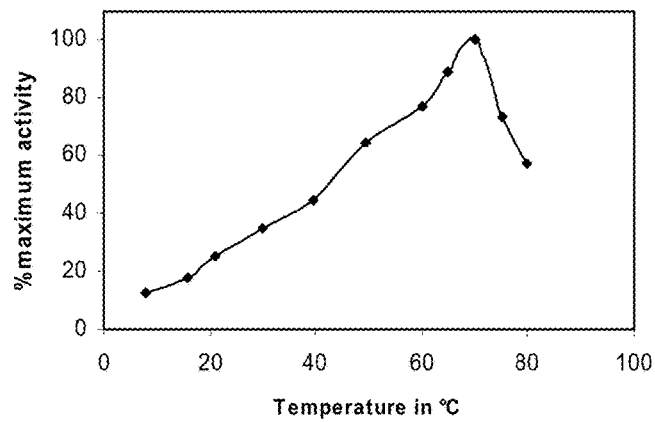
Figure 5:
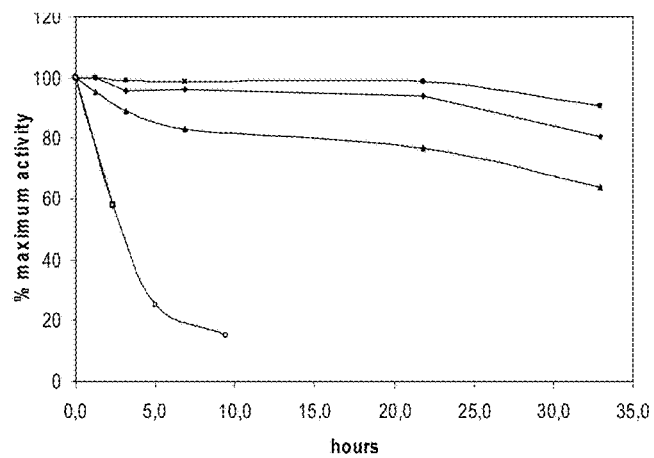

When DCPIP is used as electron acceptor, the optimal temperature for CDH is 70° C. The recombinant enzyme displayed activity over a wide range of temperatures, 16% of residual activity at 10° C. and 55% of residual activity at 80° C. (FIG. 5, A).

After incubation of CDH at 45, 50 and 55° C. for 33 h, residual enzyme activity was 90%, 80% and 63% respectively. However, CDH was not stable at 65° C., with only 15% of activity remaining after 9 h (FIG. 5, B).

The optimal pH for recombinant CDH (FIG. 5, C) was pH 4.5.

The recombinant CDH had $V_{max}$=22.2 U·mg$^{-1}$ and $K_M$=35.5 μM for DCPIP on cellobiose oxidation. Using cyt c as electron acceptor, we found $V_{max}$=3.9 U·mg$^{-1}$ and $K_M$=14.7 μM (Table 2).

TABLE 2

Apparent kinetic constants of purified rCDH for selected electron acceptors. Reactions were performed at 30° C., pH 4.5 using cellobiose as electron donor.

| Electron acceptor | $K_M$ (μM) | $V_{max}{}^a$ (μmol · min$^{-1}$ · mg$^{-1}$) | $k_{cat}$ (s$^{-1}$) | $k_{cat}/K_M$ (s$^{-1}$ · mM$^{-1}$) |
|---|---|---|---|---|
| DCPIP | 35.5 | 22.2 | 40.8 | 1148 |
| Cyt c | 14.7 | 3.9 | 7.0 | 474 |

$^a$Kinetic parameters were determined using DCPIP or cyt c as electron acceptor and cellobiose as substrate under standard assay conditions.

Effect of CDH on the Saccharification of Wheat Straw

The range of lignocellulosic enzymes found in the supernatant of *P. cinnabarinus* makes this a candidate for supplementation of the *T. reesei* cocktail for saccharification of wheat straw. We thus decided to compare the efficiency of the *P. cinnabarinus* supernatant with the purified rCDH for supplementation of industrial cocktails.

Figure 6:
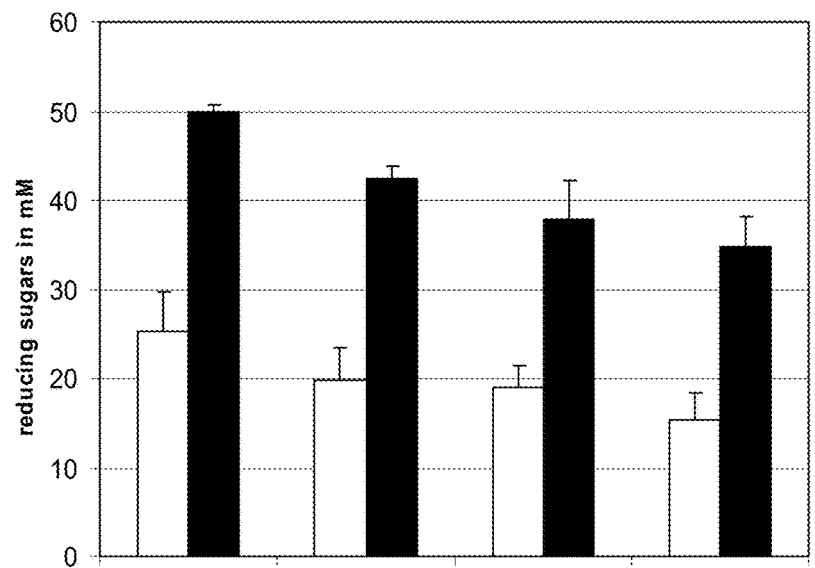
FIG. 6. Analysis of total reducing sugar yield after 96 h of enzymatic treatment on wheat straw (white bars) and pre-treated wheat straw (black bars). Experiments were conducted in triplicate and performed with *P. cinnabarinus* secretome (A) and with purified rCDH (B).
Figure 6:
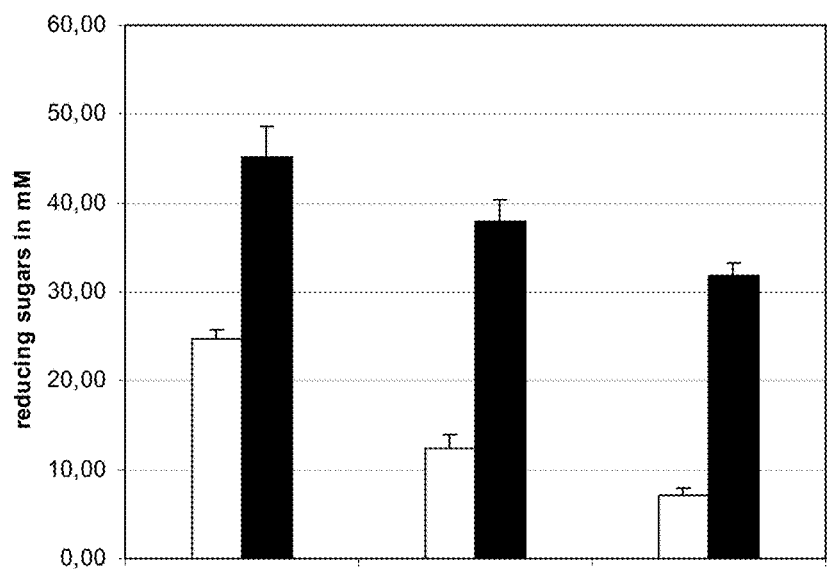
Figure 7:
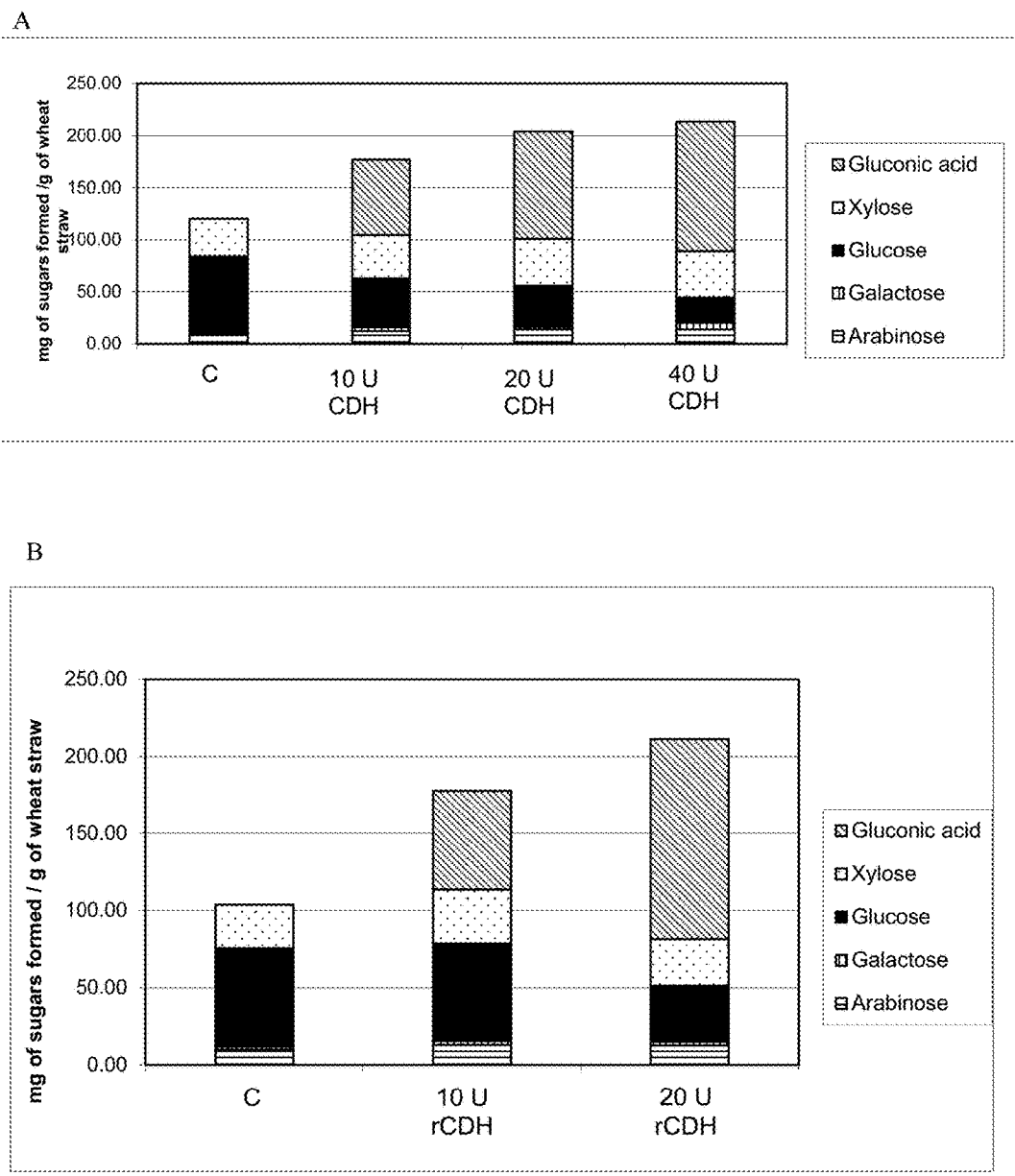
FIG. 7. Determination of sugar yield after 96 h of enzymatic treatment on wheat straw (A, B) and pre-treated wheat straw (C, D). These experiments were repeated at least three times with similar results. For all-sugars analysis in (A) and (C) statistical significance was, respectively, $P<0.1$ and $P<0.05$. In the case of (C) and (D), statistical significance was $P<0.05$.
Figure 7:
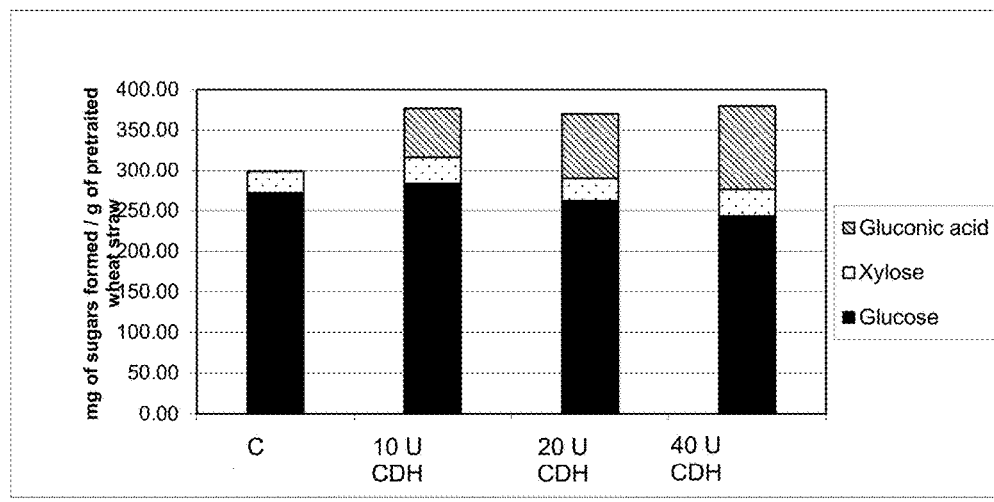
Figure 7:
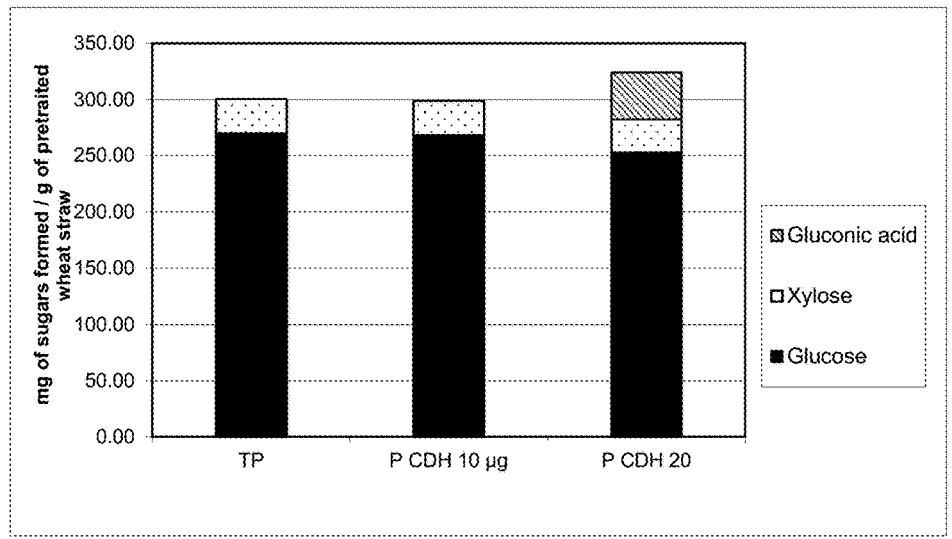

Two substrates were used: wheat straw with and without acid pre-treatment at 130° C. The *T. reesei* cocktail supplemented with β-glucosidase was used as reference Addition of *P. cinnabarinus* secretome (10, 20 and 40 U of CDH) or pure rCDH (10 and 20 U) gave similar results (FIG. 6 and FIG. 7). DNS assays were used to measure reducing ends of sugars released after saccharification. Supplementation with purified rCDH or secretome containing CDH showed less response on DNS titration than control with cocktails (FIG. 6). However, overall hydrolysis was increased by addition of CDH, with the production of large amounts of gluconic acid, from 5 to 100 mg per g of wheat straw, compared with control. Also, greater yields of xylose, galactose and arabinose, which increased respectively from 35 to 44, 1.9 to 4 and 9.5 to 13.5 mg·g$^{-1}$ of wheat straw were observed with addition of 10 U of CDH (FIG. 7, A).

Using pre-treated wheat straw (FIG. 7, C), addition of *P. cinnabarinus* secretome containing CDH resulted in (i) the production of gluconic acid up to 70 mg per gram of pre-treated wheat straw, (ii) a decrease in glucose yield and (iii) a slight increase in xylose (26 to 32 mg·g$^{-1}$).

To explain the strong production of gluconic acid, purified recombinant CDH was used to supplement the *T. reesei* and *A. niger* cocktails. The effect on wheat straw was comparable to that obtained with *P. cinnabarinus* secretome (FIG. 7, B). Also, supplementation with 10 U of rCDH did not affect the yield of glucose, increased hemicellulose yield and resulted in the formation of gluconic acid in large amounts. However, the pre-treated wheat straw did not show any marked impact of rCDH for supplementation (FIG. 7, D).

Discussion

In the *P. cinnabarinus* secretome, the inventors found hemicellulase activities already reported in the literature: α-galactosidase, xylanase or β-galactosidase, and mannosidase and arabinofuranosidase activities not hitherto described in *P. cinnabarinus*. Endoglucanase and exoglucanase were identified by zymogram (CMCase) and by hydrolysis of Avicel and CMC. Peroxidase activity assay (manganese peroxidase and lignin peroxidase) was performed on the secretome, but no activity was recovered. *P. cinnabarinus* is a well-known producer of laccase, but in cellulolytic conditions, laccase production seems repressed, whereas the zymogram shows activity on ABTS around 50 kDa. Similar results were observed in *P. chrysosporium* grown in cellulolytic condition with the presence of several laccase bands on the zymogram around 50 kDa confirmed by electron paramagnetic resonance. Production of CDH was previously described and its activity was followed in *P. cinnabarinus* culture.

The inventors cloned and expressed *P. cinnabarinus* CDH in *P. pastoris*. CDH of *T. versicolor, P. chrysosporium* and more recently *N. crassa* were previously expressed in the same host. However, the production of *P. cinnabarinus* rCDH in a 1-liter bioreactor gave the best results (7800 U·l$^{-1}$) compared with approximately 2000 U·l$^{-1}$ for the recombinant fungal CDHs cited. These results confirm that *P. pastoris* heterologous expression is an efficient way to produce fungal CDHs at high levels.

Enzymatic characterization of recombinant CDH gave values of kinetic parameters ($V_{max}$, $K_M$) in the same range as those observed previously for the native enzyme and more generally for the recombinant CDH cited in the literature.

Some CDHs produced by ascomycetes and soft-rot fungi contain a carbohydrate binding module (CBM) and are able to bind cellulose. In the case of *P. chrysosporium* CDH, the ability to bind cellulose seems to be mediated by a specific domain with a structure different from CBM (Henriksson, G., 1997, Biochem. J. 324:833-838). The ability of the purified enzyme to bind Avicel and cellulose in the absence of CBM was confirmed experimentally.

CDH is produced simultaneously with cellulase. In this work, the inventors decided to use CDH to supplement *T. reesei* cellulases and *A. niger* β-glucosidase cocktail on wheat straw.

In a first set of experiments, they used the *P. cinnabarinus* secretome containing CDH added directly to cellulase cocktail for the saccharification of two substrates: (i) wheat straw and (ii) pre-treated wheat straw by acid treatment at 130° C.

Results on wheat straw showed (i) increased yield in C5 sugars from hemicelluloses, consistent with the lignin degradation effect of the secretome, and (ii) a slight decrease in glucose yield correlated with the formation of large amounts of gluconic acid. Similar results were observed to a lesser extent on pre-treated wheat straw.

Supplementation with purified rCDH gave similar results on wheat straw and even no decrease in glucose yield, but gluconic acid and C5 sugar hemicellulose production was enhanced for 10 U CDH supplementation. Results point to synergy between CDH and cellulases for degradation of raw material. However, using pre-treated wheat straw CDH action was less striking. Pre-treated wheat straw was only slightly affected by adding rCDH to the cocktail.

In *P. cinnabarinus* secretome, β-glucosidase activity was significantly detected (Table 1). However, when no β-glucosidase was added to the saccharification assay, more cellobionic acid was produced instead of gluconic acid by *T. reesei* cocktail supplemented with *P. cinnabarinus* secretome (data not shown). It is well established that β-glucosidases are inhibited by gluconolactone and more generally that lactones are inhibitors of many glycosidases. Nevertheless, sugar lactones are unstable in aqueous solution, and the rate of spontaneous hydrolysis to the corresponding aldonic acid, i.e. gluconic acid or cellobionic acid, depends on the pH and temperature of the reaction. Aldonolactonase, found in several fungi, catalyzes hydrolysis of lactones to aldonic acid. This hydrolysis should relieve inhibition of β-glucosidase and glycosidase for lactone. β-Glucosidase is able to cleave cellobionic acid into glucose and gluconic acid; cellobionic acid and gluconic acid production decreases the number of reducing ends as shown by the decrease in DNS titration. In the presence of CDH, DNS titration is not a relevant method for monitoring cellulose degradation. This could be explained by the oxidation of cellodextrine ends, DNS response decreasing as CDH concentration increased. The presence of cellobionic acid seems due to a faster reaction rate of CDH than β-glucosidase versus cellobiose, as shown by Yoshida et al. (2004, FEMS Microbiol. Lett. 235:177-182).

Supplementation with β-glucosidase compensates for the difference in reaction rate, leading to a greater production of gluconic acid. Conversely, as the accumulation of cellobiose induces inhibitory effects on cellulase, CDH may decrease the cellobiose concentration in the medium faster and so avert inhibition.

Dumonceau et al. demonstrated that CDH was essential for *T. versicolor* to colonize wood, but has no significant effect on delignification of Kraft pulp (2001, Enzyme Microb. Technol. 29:478-489). Although the oxidizing system of CDH is still not completely understood, production of oxidative compounds such as $H_2O_2$ seems essential for the degradation of lignocellulose. In the absence of peroxidase in *P. cinnabarinus* secretome, the heme part of CDH should be able to carry out a Fenton-type reaction with $H_2O_2$ and generate hydroxyl radicals that could be a key component of lignocellulose breakdown.

Example 2

Production of Sugars—Determination of Sugar Yield in Mg of Sugars Formed/g of Beechwood Xylan after 72 h of Enzymatic Treatment on Xylan Saccharification assays were performed in 20 mL of 50 mM sodium phosphate buffer (pH 4.8) containing 5% (w/v) beechwoodxylan.

Purified rCDH was assayed in the presence of cellulase cocktail at 45° C. with an orbital agitation (140 rpm) during 72 h.

C: control reaction was performed with GC 220 containing xylanase activity without CDH. Sugars were quantified by high-performance anion exchange chromatography (HPAEC) coupled with amperometric detection (PAD) equipped with a Carbo-Pac PA-1 analytical column These experiments were repeated at least three times with similar results. For all-sugars analysis statistical significance was P<0.05 respectively. The results are shown on FIG. 8.

GC220 (Genencor-Danisco, Rochester, N.Y., USA) from *T. reesei* contained 1.41 U CMCase, 0.79 U β-glucosidase, 0.11 U cellobiohydrolase, 3.85 U xylanase, 0.26 U mannanase, 0.14 U pectinase per mg of total protein. 120 µl of GC 220/g of xylanbeechwood. Protein concentration is 69 µg/µl.

Figure 8:
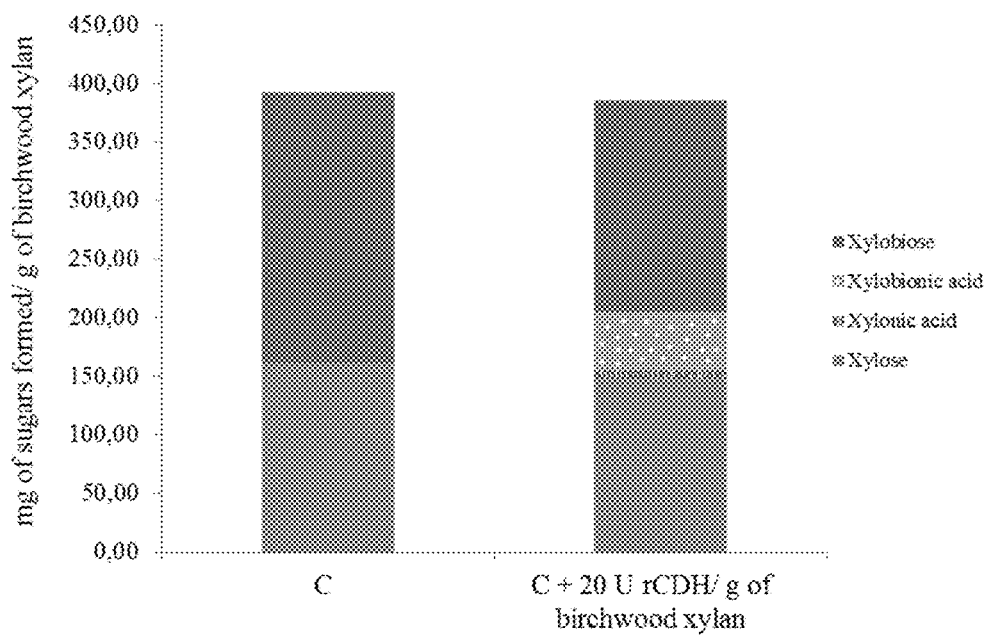
FIG. 8. Determination of sugar yield in mg of sugars formed per gram of beechwood xylan after 72 hours of enzymatic treatment on xylan.

FIG. 8 shows an increase in the sugars production compared to the control, more particularly an increase of production of xylobionic acid and xylonic acid.

Example 3

Synergistic Action of Cellobiose Dehydrogenase from *Pycnoporus cinnabarinus* and GH161 from *Podospora anserina*

In this work, we used a combination of CDH from the basidiomycete *Pycnoporus cinnabarinus* and two GH61 from the brown-rot ascomycete *Podospora anserina* both heterologously expressed in *Pichia pastoris*. Synergistic action enzymes are observed on PASC.

Materials and Methods

Biological Material

*P. anserina* strain S mat+ was provided by Pr. P. Silar (UMR 8621 CNRS, Orsay). Heterologous expression of rCDH from *P. cinnabarinus* ss3 monokaryotic strain BRFM 137 was described in Bey et al (2011, Microbial Cell Factories, 10:113). *P. pastoris* strain X33 and the pPICZαA vector are components of the *Pichia* Easy Select Expression System (INVITROGEN).

Media and Culture Conditions

*P. anserina* S mat+ was grown at 27° C. on M2 plates ($KH_2PO_4$: 0.25 g/l; $K_2HPO_4$: 0.3 g/l; $MgSO_4.7H_2O$: 0.25 g/l; urea: 0.5 g/l; thiamine: 0.05 g/l; biotin: 0.25 µg/l; citric acid: 2.5 mg/l; $ZnSO_4$: 2.5 mg/l; $CuSO_4$: 0.5 mg/l; $MnSO_4$: 125 µg/l; boric acid: 25 µg/l; sodium molybdate: 25 µg/l; iron alum: 25 µg/l; dextrin: 5 g/l; yeast extract: 10 g/l; agar: 12.5 g/l and pH was adjusted to 7 with $KH_2PO_4$). Precultures in Roux flasks containing 200 ml of M2 medium without agar supplementation were inoculated by five disks (0.5 cm in diameter) of *P. anserina* grown in M2 plates. Inoculum was obtained from 5-day-old static precultures incubated at 27° C. Inoculum suspension was obtained from seven mycelial mats ground with Ultra-Turrax in 200 ml of water. Ten ml were used to inoculate 500 ml baffled conical flasks containing 100 ml of M2. For the heterologous expression of PaGH61 in *Pichia pastoris*, all media and protocols are described in the *Pichia* expression manual (INVITROGEN).

Isolation of mRNA and Cloning of gh61 cDNA Gene

From M2 culture plate of *P. anserina*, a 1 mm-square of agar is placed in 500 µl of dd$H_2O$ and ground with Fastprep (MP BIOMEDICALS) during 30 s. The suspension obtained was used to inoculate roux flasks containing 200 ml of M2. The mycelium was harvested after 7 days cultures at 27° C. and frozen in liquid nitrogen and ground with mortar. Extraction of genomic DNA was realised with wizard DNA genomic DNA kit according to manufacturer (PROMEGA).

Isolation of total RNA was performed on a 3 to 8-day-old culture of *P. anserina* on cellulose or xylan medium using Total RNA Purification from Plant (MACHEREY-NAGEL) as prescribed by the manufacturer. The mRNA of *P. anserina* was purified from the total RNA using mRNA Isolation kit from Roche following standard protocol. Contaminant DNA was digested by Turbo DNase (AMBION INC.) according to the manufacturer's instructions. First-strand cDNA synthesis was performed using SuperScript reverse transcriptase (INVITROGEN) and oligo ($dT_{18}$) primer following the manufacturer's instructions. The amplification of the full-length Pagh61B, Pagh61A and Pagh61E cDNA was performed using specific primers (vector-specific part is underlined) using the Clontech In-Fusion® PCR Cloning System (TAKARA BIO INC.) to fuse the ends of the PCR fragment to the homologous ends of linearized pPICZαA (INVITROGEN). Primers designs were performed using In-Fusion® Primer Design Tool: forward primer PaGH61B F: (SEQ ID No6) (5' <u>AGGGGTATCTCTCGAGA-AAAGAC</u>ATTCCACCTTCCAACAGC 3') and the reverse primer PaGH61B R: (SEQ ID No7) (5' <u>GAGTTTTTGTTCTAGA</u>CCCACGCACTGGTGATACCA 3') designed from *P. anserina* S mat+ GH61B gene (NCBI gene id: CAP68375.1); forward primer PaGH61A F: (SEQ ID No8) (5' <u>AGGGGTATCTCTCGAGA-AAAGAC</u>ACGGCCACGTCTCCC 3') and the reverse primer PaGH61A R: (SEQ ID No9) (5' <u>GAGTTTTTGTTCTAGA</u>CCGATGCACTG-GCTGTAGTAAG 3') designed from *P. anserina* S mat+ gh61A gene (GenBank: CAP 73254.1); Primers designs were performed using In-Fusion® Primer Design Tool: forward primer PaGH61E F: (SEQ ID No10) (5' <u>AGGGGTATCTCTCGAGA-AAAGAC</u>ACTCCATCTTCCAA-AAGGTG 3') and the reverse primer PaGH61E R: (SEQ ID No11) (5' <u>GAGTTTTTGTTCTAG</u>-ACCTGTACTACCGCCTGG 3') designed from *P. anserina* S mat+ GH61E gene (GenBank: CAP61476.1) Amplification was realised by Expand high fidelity PCR system accordingly with manufacturer's instructions (ROCHE). The reaction was performed following the amplification program: 1 cycle at 94° C. for 2 min, 30 cycles composed of three steps for each cycle (94° C. for 15 s; 58° C. for 30 s and 72° C. for 55 s), and a final step of 72° C. for 7 min The PCR product was fused with pPICZα-A vector linearized using EcoRI and XbaI and purified with a Qiaquick gel extraction kit. The Pagh61A/B/E cDNA was further sequenced (GATC BIOTECH) using specific design primers.

Transformation and Screening

Transformation of competent *P. pastoris* X33 was performed by electroporation with PmeI linearized pPICZα A-PaGH61B/A/E. The vector pPICZα without insert was used as a control. Transformants were first screened on YPDS plates with different concentrations of zeocin (100 to 1000 µg/ml). After incubation at 30° C., transformants were picked from minimal dextrose (MD) plates and transferred to minimal methanol plates (MM). Zeocin-resistant *P. pastoris* transformants were then screened for protein expression in 10 ml of BMGY (in 50 ml tubes) at 30° C. in an orbital shaker (200 rpm) for 16 h to an $OD_{600}$ of 2-6, and expression was induced by transferring cells into 2 ml of BMMY and grown for another 3 days. Each day the medium was supplemented with 3% (v/v) methanol. The supernatant was then analyzed by SDS-PAGE to determine the transformant with the best secretion yield.

Production of Recombinant Enzymes

The best-producing transformant was grown in 1 liter of BMGY in shaken flasks as described above. The cells were then transferred to 200 ml of BMMY and stirred at 200 rpm and 30° C. for 4 days. Bioreactor production of the best-producing transformant was carried out in a 2-liters bioreactor Tryton according to the *Pichia* Fermentation Process Guidelines (INVITROGEN). The production of recombinant enzymes produced in *P. pastoris* was performed in 2-liters bioreactor. First, precultures were realised in 0.5 liter shake flask containing 100 ml of BMGY medium (10 g/l of yeast extract, 20 g/l of peptone and 10 g/l of glycerol). After 60 hours of growth at 28° C. under shaking at 130 rpm, 50 ml of preculture was used to inoculate the bioreactor to reach the DO 600 to 1.0.

The basal salts medium used for the batch phase (phase I) in bioreactor was composed by 40 g/l of glycerol; 26.7 ml/l $H_3PO_4$, 14.9 g/l $MgSO_4 \cdot 7H_2O$, 0.93 g/l $CaSO_4$, 7.7 g/l KCl, 4.13 g/l KOH, 4.35 ml/l $PTM_1$ salt solution.

Batch phase was performed at 30° C. with agitation of 600 rpm and pH controlled at 5.0 with ammonium hydroxide (28%, v/v). The total $O_2$ flow was kept constant at 0.3 vvm. After 20-24 h on batch phase, the second phase consisted in 50 g addition of sorbitol simultaneously with 0.5% methanol (v/v) to the bioreactor until yeasts were adapted to methanol metabolism (i.e. 3 h later). Induction phase (phase III) was carried out for 72 h. Methanol added during the latter phase contained 12 ml/l of $PTM_1$ salts and was added to 5 ml/h under 800 rpm to stay in 20% of dissolved oxygen in the bioreactor.

For rCDH production, the phase III temperature was 30° C. This temperature was decreased to 25° C. for the producing of rPaGH61A/B to ensure well maturation of proteins.

Enzyme Purification

Culture supernatant was concentrated at least 10 times using Amicon centrifugal units with a 30 kDa cut-off, 4000×g or Amicon vivaflow (MILLIPORE) with a 10 kDa cut-off depending on culture volume. The concentrated supernatant was dialyzed against buffer A (Tris-HCl 50 mM 7.8, NaCl 150 mM, imidazole 10 mM) and loaded on a nickel chelate His-Bind Resin (GE HEALTHCARE) column (0.7×5 cm) connected to an Äkta FPLC (GE HEALTHCARE) and equilibrated with buffer A. His-tagged recombinant enzymes were eluted with buffer B (Tris-HCl 50 mM pH 7.7, imidazole 500 mM, NaCl 150 mM). Fractions containing recombinant enzyme (active fraction for rCDH and SDS-PAGE determination for rPaGH61) were pooled, concentrated and dialyzed against HEPES-NaCl buffer (HEPES 20 mM, NaCl 150 mM) pH 5. Samples were purified on Sephacryl 200 HR column (GE HEALTHCARE) using the same buffer. Fractions corresponding to core of the peak and exhibiting presence of recombinant enzymes were pooled and dialyzed against sodium acetate buffer 50 mM, pH 4.8.

Protein Analysis

Polyacrylamide gel electrophoresis (SDS-PAGE) (12%) was prepared as described by Laemmli. Protein bands were stained with Coomassie blue G 250. The molecular mass under denaturating conditions was determined with reference standard proteins (Pageruler Prestained Protein Ladder, Thermo Fisher Scientific).

Enzyme activities were assayed in polyacrylamide gels containing the appropriate substrates. Enzyme preparations were run on a PAGE gel copolymerized with 0.4% carboxymethylcellulose (CMC). The protein samples were mixed in the loading buffer (1% SDS w/v; 30% saccharose w/v; 30 mM Tris-HCl buffer pH 6.8) without reducing agent before separating using a 12% polyacrylamide gel. After electrophoresis, the gel was soaked in 50 mM sodium phosphate buffer (pH 5) containing 10 mM of ascorbic acid and incubated overnight at 45° C. under shaking. After incubation the gel was stained with 0.1% Congo red solution under gentle shaking for 1 h and destained with 1M NaCl for 1 h. Protein bands exhibiting GH61 activity on CMC were observed as clear bands on the red background.

Protein Determination

Protein concentration was determined using the Bio-Rad Protein Assay (Bio-Rad, Marnes-la-Coquette, France), based on the Bradford procedure, using bovine serum albumin as standard.

Enzyme Assays rCDH activities were determined by monitoring the reduction of 0.2 mM 2,6-dichlorophenol indophenol (DCPIP) in 100 mM sodium acetate buffer (pH 4.8) containing 10 mM cellobiose. The decrease in absorption at 520 nm ($\epsilon = 6800$ $M^{-1} \cdot cm^{-1}$) was monitored at 30° C. for 1 min. Enzyme activity was expressed in international units (IU). One unit of activity is defined as the quantity of enzyme that transforms 1 μmol of substrate in one minute. All assays were performed in triplicate.

Cellulose Cleavage Assays

Cleavage assays were performed in 50 ml Falcon tubes (BD BIOSCIENCE) containing 1% (w/v) PASC in 50 mM sodium phosphate buffer (pH 4.8) in a final reaction volume of 10 ml. PASC was prepared as described by Wood et al. (1988, *Methods Enzymol* 1988 160: 19-25). Purified enzymes (rCDH, rPaGH61A and rPaGH61B) were added to the basal medium described above at different concentrations: 500 μg/g for rCDH, 5 and 50 mg/g for rPaGH61. Assays were performed in incubators (INFORS AG) at 45° C. with an orbital shaker (140 rpm) for 48 h. After 48 h of incubation, all the samples were centrifuged at 3500 rpm for 15 min. The supernatants were filtered through a 0.20 μm membrane before carbohydrate determination. Saccharification assays were performed in triplicate.

Carbohydrate Determination

Mono-, oligosaccharides and their corresponding aldonic acid forms generated after PASC cleavage were identified by high-performance anion exchange chromatography (HPAEC) as described by Forsberg et al. (2011, *Protein science.*, 20:1479-1483). All the assays were carried out in triplicate. Product analysis by mass spectrometry was realized with an Ultraflex II MALDI-TOF/TOF instrument (BRUKER DALTONIC GMBH) with 200 Hz smartbeam laser. Analysis conditions were previously described by Vaaje-Kolstad et al. (2010, *Science*, 330 (219): DOI: 10.1126/science. 1192231).

Results

Heterologous Expression of GH61A and GH61B from *P. anserina* in *P. pastoris*

Figure 9:
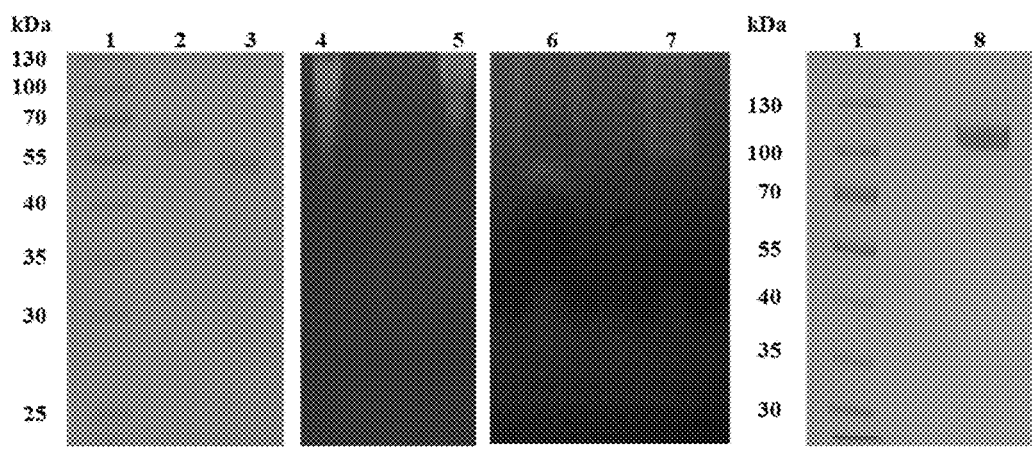
FIG. 9. SDS-PAGE and zymogram analysis of rPaGH61. SDS-PAGE: lane 1, prestained molecular weight marker; lane 2, 10 µg of purified rPaGH61A; lane 3, 10 µg of purified rPaGH61B; lane 8, 10 µg of purified rCDH. Zymogram CMC on Native condition (w/o heating) incubated overnight at 45° C. under shaking with addition of 10 mM of ascorbic acid: lane 4, 50 µg of rPaGH61B; lane 5, 50 µg of rPaGH61A. Zymogram CMC with 5 min heating incubated in the same condition than described above: lane 6, 150 µg of purified rPaGH61B; lane 7, 150 µg of purified rPaGH61A.

Three genes encoding PaGH61 (PaGH61A (Genbank CAP73254.1) of SEQ ID No12, PaGH61B (Genbank CAP68375.1) of SEQ ID No13 and PaGH61E (Genbank CAP61476.1) of SEQ ID No14) from *P. anserina* were cloned into pPICzαA for subsequent expression in the yeast *P. pastoris*. Although we were not able to detect any PaGH61E protein in the supernatant of selected *P. pastoris* transformants following induction, PaGH61A and PaGH61AB were successfully expressed in *P. pastoris* and further produced in bioreactor. PaGH61A and PaGH61B were produced to high yield since we obtained 150 mg and 1 g of each protein per liter of culture, respectively. Electrophoretic analysis revealed that purified PaGH61A and PaGH61B displayed apparent molecular masses of 60 and 50 kDa, respectively (FIG. 9, lane 2 and 3). In parallel, production of recombinant CDH was conducted as described by Bey et al as disclosed previously.

Zymogram Containing CMC Revealed Activities for rPaGH61A and rPaGH61B

In order to observe endoglucanase activity of PaGH61A and PaGH61B, we performed zymogram analysis with addition of CMC into the gels (FIG. 9). When the gel was carried out under native conditions and incubated with ascorbic acid, clear halos were visualized at the top of the gel (FIG. 9, lanes 4 and 5). When zymogram was carried out under denaturing conditions and incubated with ascorbic acid, halos were visualized at molecular masses corresponding to PaGH61A and PaGH61B (FIG. 9, lanes 6 and 7) but with less intensity.

Synergy Between rCDH and rPaGH61

We performed PASC cleavage assays to investigate synergy between GH61 from *P. anserina* and rCDH from *P. cinnabarinus* both expressed in *P. pastoris*. The products formed by cellulose cleavage were further analyzed using HPAEC (FIG. 10) and the corresponding mass spectrometry analysis was shown in FIG. 11. Identifications of each peak were realized on the basis of the m/z.

Figure 10:
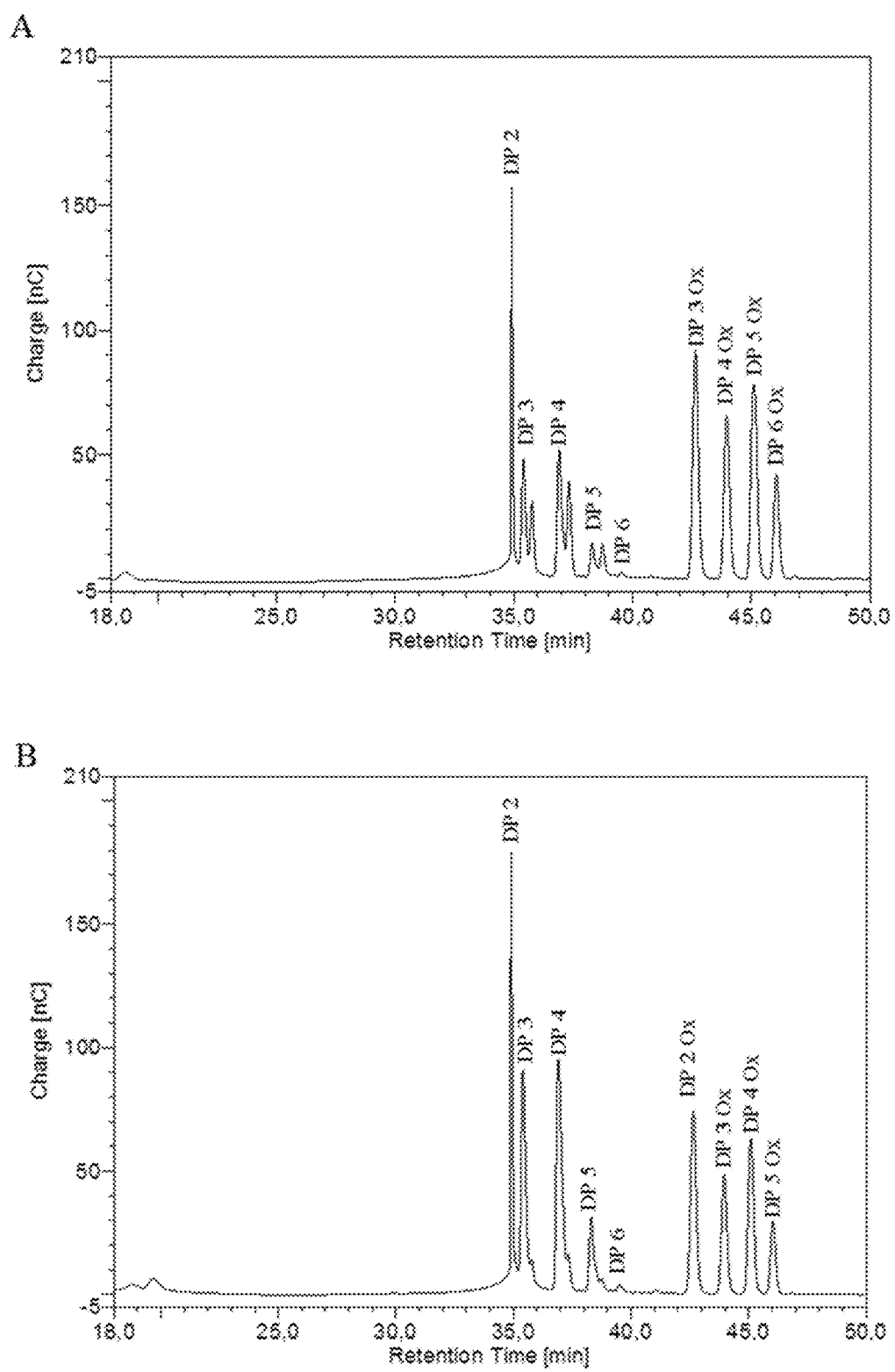
FIG. 10. Products generated during PASC cleavage. Analysis with HPAEC showed chromatograms obtained after 48 h incubation at 45° C. under shaking of 1% (w/v) PASC in 50 mM sodium acetate pH 5 with rCDH/rPaGH61. Chromatogram A represents action of rPaGH61A at 5 mg/g and panel B shows action of 5 mg/g of rPaGH61B, both of them are in association with 500 µg/g of rCDH. Chromatogram C shows products formed by combination of rPaGH61B (50 mg/g) with 500 µg/g of rCDH. All experiments were realized in triplicates.
Figure 10:
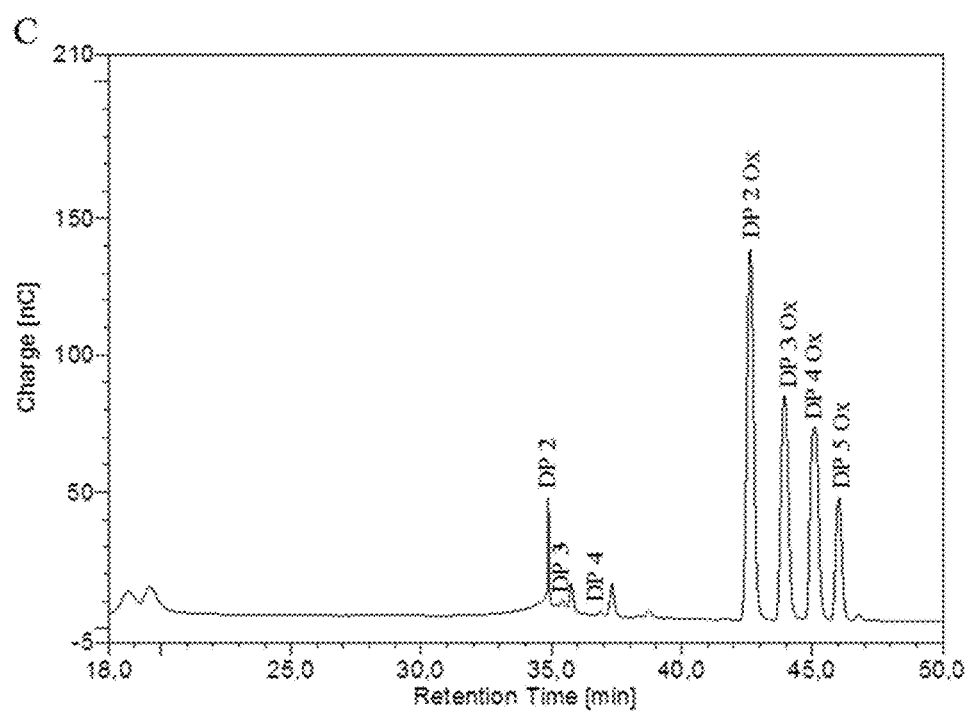
Figure 11:
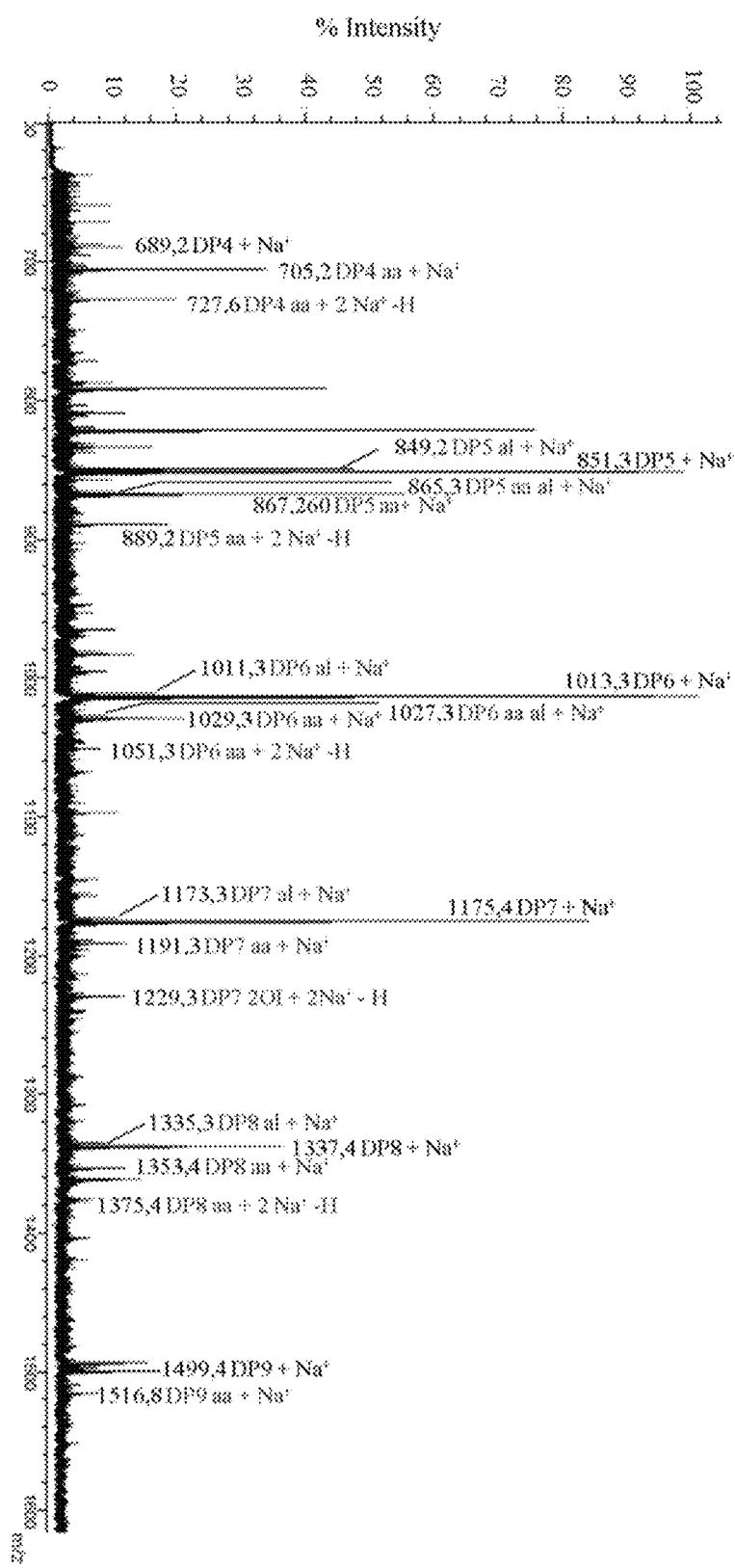
FIG. 11 MALDI TOF/TOF spectrum of products released by the combination of rCDH (500 µg/g) and rPaGH61A (5 mg/g) after 48 h incubation at 45° C. under shaking of 1% (w/v) PASC in 50 mM sodium acetate pH 5. In the same conditions, recombinant CDH (500 µg/g) was added to 5 mg/g (B) or 50 mg/g of rPaGH61B (C). MS/MS fragmentation was performed on product released at m/z=1245 during the same condition than previously described for panel C (D). Identified compounds are black labelled for native cellodextrins and red labelled when the products are oxidized. aa=aldonic acid; al=aldonolactone/lactone; OI=oxygen incorporation *=compounds marked are subject to hypothesis.
Figure 11:
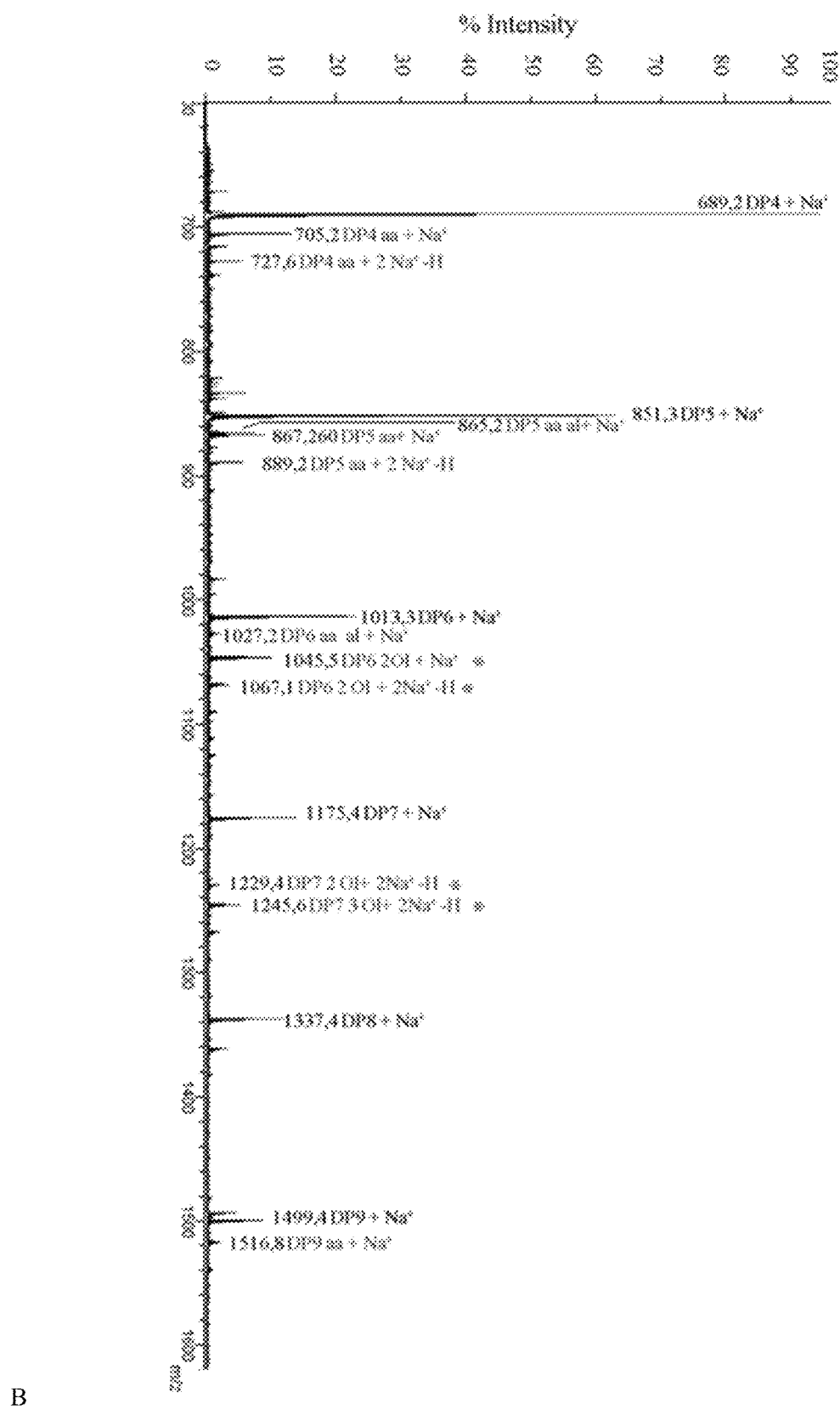
Figure 11:
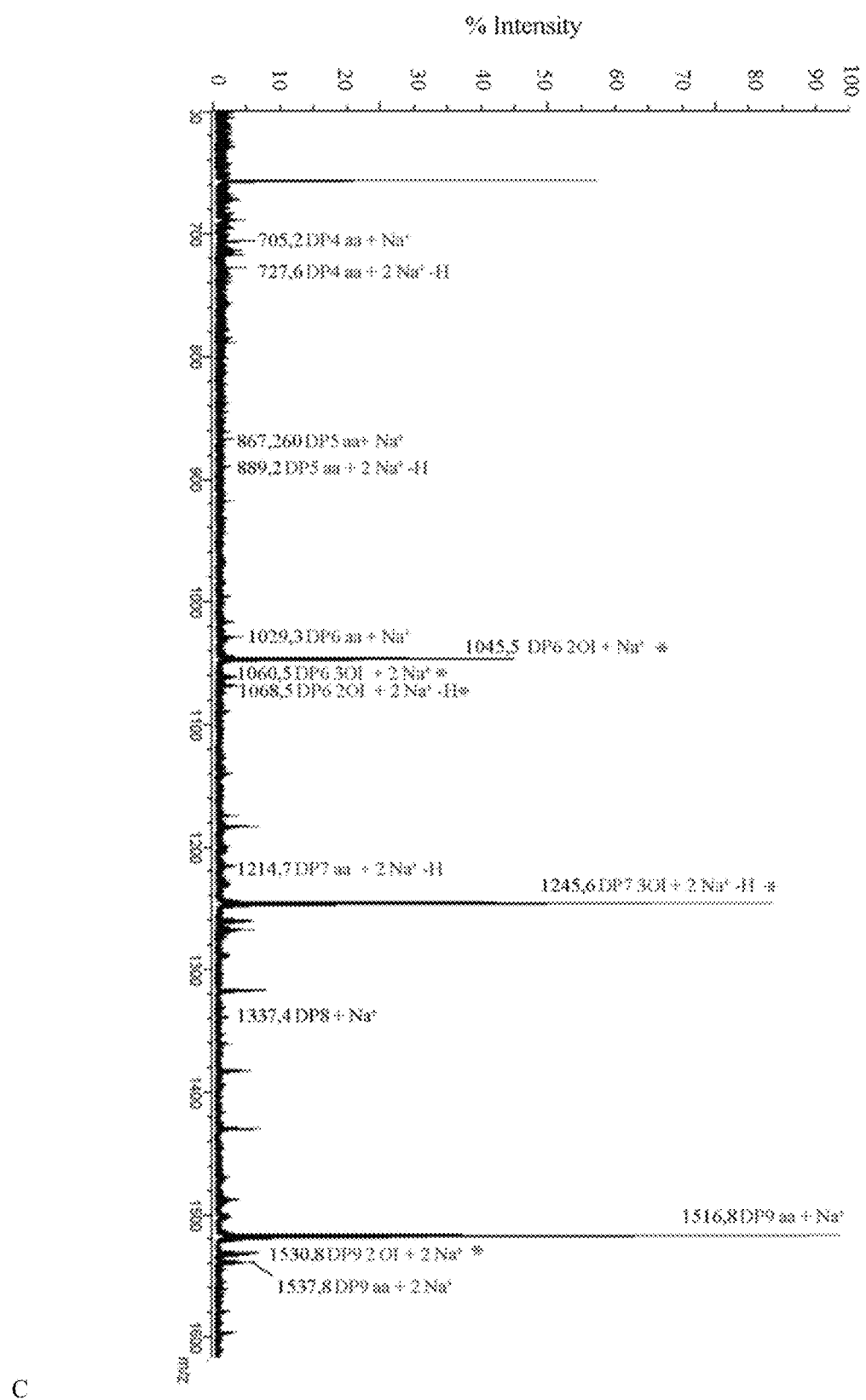
Figure 11:
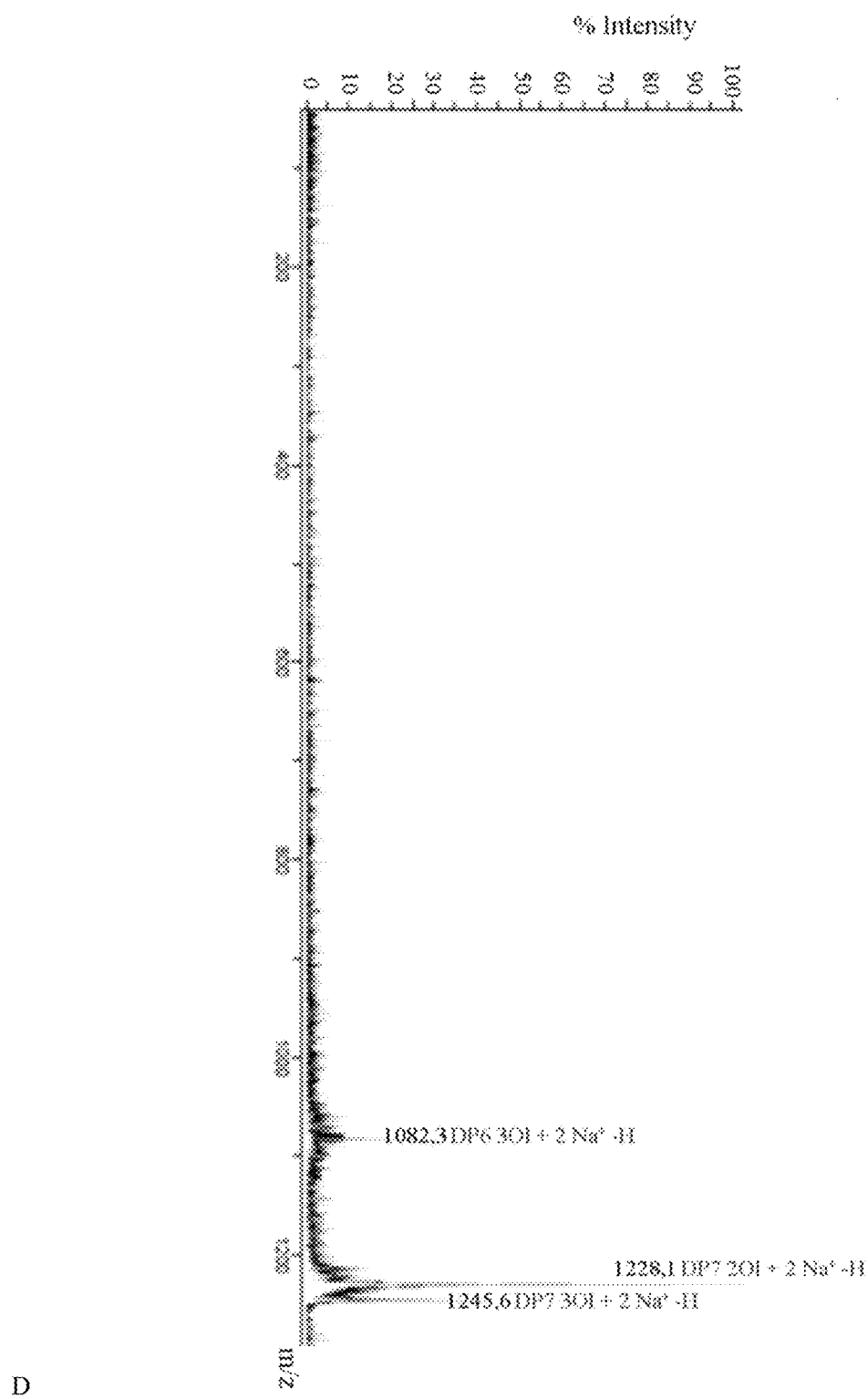

FIG. 10A shows HPAEC analysis of compounds produced when rPaGH61A was incubated with rCDH on amorphous cellulose. Chromatogram exhibits release of cello-oligosaccharides oxidized and non-oxidized as well as peaks close to native cellooligosaccharides and identified as corresponding lactone (m/z−2) by mass spectrometry (FIG. 11, A). Presence of oxidized cellodextrins (m/z+16) was confirmed by mass spectrometry and detection of compounds consistent with double oxidation could explain masses corresponding to m/z+14 (for DP 5 and 6) supporting a C4 oxidation by rPaGH61A. The presence of oxidized compounds are less represented than observed on HPAEC due to the presence of cations from acetate buffer (association of oxidized compounds with $Na^+$ or $2\ Na^+$) (FIG. 11A).

To investigate difference between the two rPaGH61, rCDH was also combined with rPaGH61B in the same condition than previously used for rPaGH61A. Analysis of products generated by this combination revealed formation of cello-oligosaccharides (DP 2 to 6) oxidized and non-oxidized as well as corresponding lactones (m/z−2) represented as shoulder as the native cellodextrins peaks (FIG. 10, B). The predominant form was represented by non-oxidized cello-oligosaccharides whereas oxidized compounds were present in less extent such as lactone intermediates. Confirmation was carried out by mass spectrometry where spectrum shows formation of native compounds with predominance going to low DP (DP 4, 5, 6), non-oxidized compounds were less represented than previous experiment with rPaGH61A.

In addition to these differences, few lactone intermediates were identified in mass spectrometry but products with m/z+14, assimilated to double oxidation (in C1 and C4 position) has been detected in MALDI TOF/TOF leading to the same hypothesis exposed for rPaGH61A (FIG. 11A).

Among oxidized compounds released during rCDH/rPaGH61B synergy, two peaks, absents in the previous experiment, were observed at m/z=1045 and m/z=1245. The product corresponding to m/z=1045 could be explain by combination of oxidation such as doubly oxidized DP6 (m/z+32) with $Na^+$ adduct (m/z+23). Product at m/z=1245 is consistent with triple oxidation of DP7 (m/z+48) with 2 $Na^+$—$H^+$ (m/z+47). Such compounds could represent new type of oxidation. Indeed, identification of high masses corresponds to cello-oligosaccharides with two oxidations or more leading to multiple incorporation of oxygen molecule. The first oxidation appears on reducing end (C1 position) and the second at the non-reducing end or along the cellulose chain until cleavage of glycosidic bond (see FIG. 12).

To highlight this phenomenon, concentration of rPaGH61B has been enhanced and associated with rCDH. FIG. 10 C presents chromatogram showing products released by this synergy. As expected, high concentration of rPaGH61B leads to formation of oxidized cellodextrins, mostly present compared to non-oxidized cellodextrins and their lactones forms (FIG. 10 D). In FIG. 11 C, mass spectrometry supports these observations and the previous hypothesis, revealing exclusively the formation of oxidized compounds with an enhancement of peaks corresponding to m/z=1045 and m/z=1245. MS/MS fragmentation of these two products has been performed and reveals the presence of compounds such as DP5 and DP6 with multiple oxidations (according to masses) respectively for m/z=1045 (DP6) and m/z=1245 (DP7). Results could be explained by modification into the chain and not necessarily at the reducing and non-reducing ends.

Discussion

Oxidative reactions are interesting field of investigation to solve the problem caused by substrate recalcitrance during enzymatic hydrolysis performed by cellulases. Indeed, hydrolytic enzymes used for lignocellulose degradation are sensitive to substrate accessibility and high cost of enzymatic cocktail is problematic.

To unlock this situation, different ways were investigated such as the action of glycosyl hydrolase family 61 acting as polysaccharide monooxygenase, which depends on the presence of reducing agents such as organic acids (ascorbate, gallate, etc. . . . ), lignin components or cellobiose dehydrogenase. Association of these two enzymes leads to cellulose cleavage by oxidative mechanisms. *Podospora anserina* represents an interesting tool for new targets discovery because genome analysis of the cellulolytic fungi revealed the presence of 33 genes encoding putative GH61. Among these, three of them were selected to be expressed in *P. pastoris*: PaGH61A, PaGH61B and PaGH61E. Choice was based on the presence of CBM family 1, representing putative activity on cellulose and representativeness of different families of GH61 even if their presences were not essential for activity. Two genes (Pagh61A and Pagh61B) were successfully express confirming that expression system based on *P. pastoris* is efficient for heterologous expression of GH61. SDS-PAGE (FIG. 9, lane 2 and 4) reveals molecular weights of rPaGH61 similar to those previously described and showed high glycosylation of enzymes due to *P. pastoris* expression. Expression yield was relatively high (ie. 1 g/L for rPaGH61B production in bioreactor) considering high quantities required for experiments. To date, measurement of GH61 activity was not defined.

Here, we described method based on CMCase zymogram using ascorbate as reductant. The presence of discolorations corresponding to GH61 action on CMC under denaturating and non-denaturating conditions supports efficiency of zymogram method to observe GH61 integrity.

To confirm these observations, we performed PASC cleavage assays using rCDH and rPaGH61. Synergistic action revealed formation of cellooligosaccharides oxidized and non-oxidized with both rPaGH61 (FIGS. 10 and 11, A, B, C). As already reported, results reflect oxidative reaction when rCDH and GH61 were incubated simultaneously on amorphous cellulose. Apparition of compounds such as native cellodextrins could take origins in oxidative cleavages near to reducing ends releasing intact non reducing moiety. Controls containing rPaGH61 or rCDH incubated on PASC at the same concentration used during proposed experiments without any reductant produced only traces of non-oxidized (for rPaGH61) or oxidized (for rCDH) compounds (data not shown).

When rCDH has been associated with rPaGH61A and rPaGH61B, different behaviors were observed whereas these two enzymes are susceptible to belong to PMO type 3 family such as HjCel61B and TaGH61A. It has been suggested that PMO-3 realized oxidation of cellulose with less specificity than PMO-1 (oxidation in C1 position) and PMO-2 (oxidation in C4 position). Concentrations of oxidized compounds products in both cases were relatively close (FIGS. 10 A and B) compared to non-oxidized cellodextrins. Peaks corresponding to lactone formation appeared as shoulders of the non-oxidized cellooligosaccharides peaks for rPaGH61B while rPaGH61A exhibited an accentuated presence of lactone intermediates. Presence of such products could be explained by C4 oxidation and were supported by the detection of compounds with masses consistent to a double oxidation composed by m/z+16 and ketone (m/z−2).

Significant difference concerns the enhancement of native cellooligosaccharides (especially for low DP) produced by rPaGH61B/rCDH combination. Another difference was observed by identification of two products (m/z=1045 and m/z=1245) released during the same enzymatic association, among oxidized cellodextrins, cellooligosaccharides exhibits masses consistent with double or triple oxidation (at C1, C4 or C6 position) confirming the possibility that rPaGH61B (assimilated to PMO-3) could process with less specificity. It has been proposed that products such as m/z=1245 could result to ketal formation from 4-keto sugar.

Figure 12:
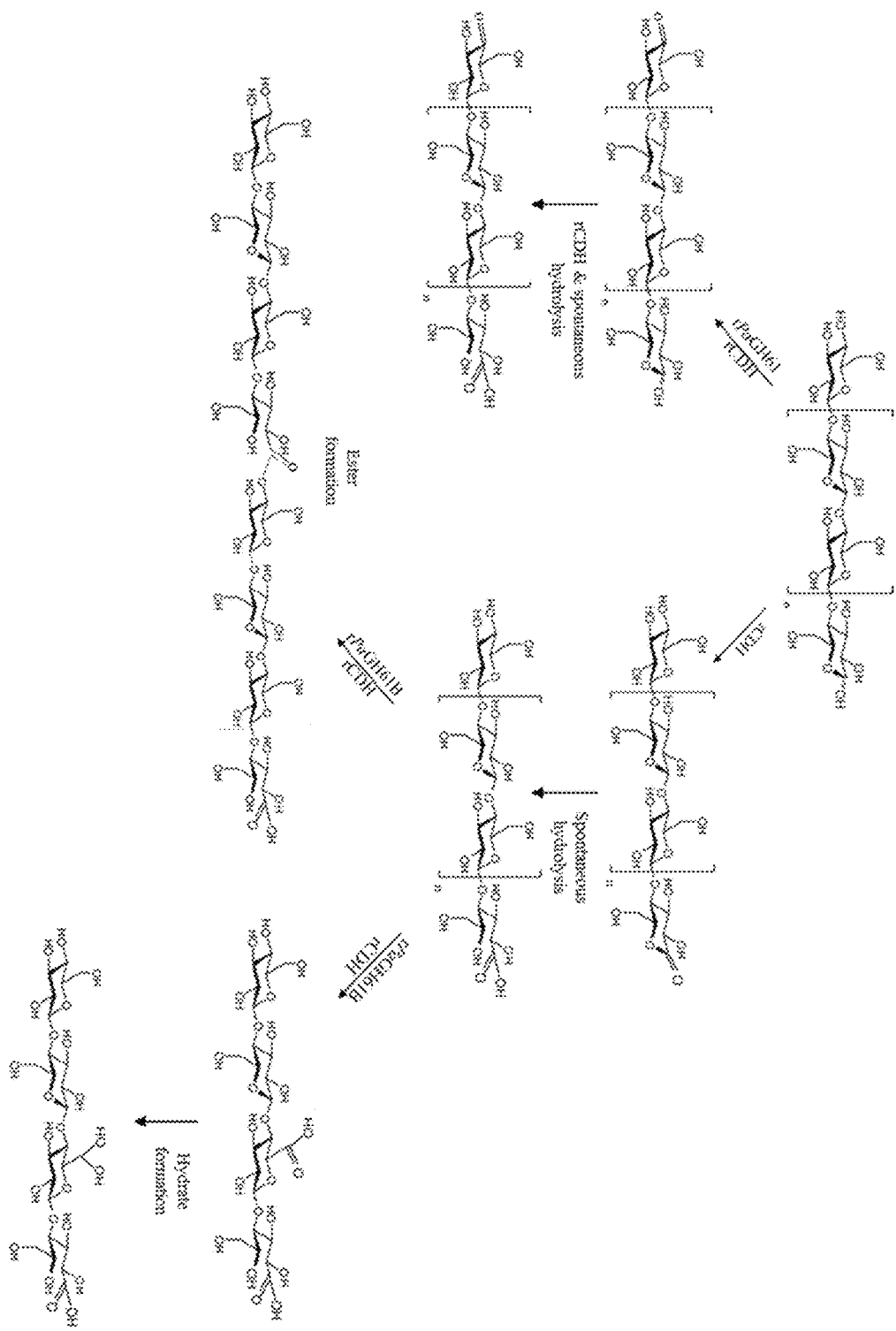
FIG. 12 Schematic representation of products formed by the synergistic action of rPaGH61 and rCDH. Cellooligosaccharides were oxidised at C1 position or multiple oxidations (ketal on C6 position or ester formation).

However, oxidation in C6 position is more probable, leading to carboxylate group and subsequent ketal formation at C6 (FIG. 12). MS/MS fragmentation shows masses consistent with triple oxidations for DP7 compounds and its subsequent DP6 fragment leading to conclusion that oxidation could occur in other place that non reducing end. Results are supported by compound with masse corresponding to triple oxidation. Another hypothesis based on ester formation on cellulose could explain such masses. Indeed, after hydrogen abstraction at C1 position, the subsequent addition of oxygen atom at the same position could be stabilize by ring cleavage and ester formation (see FIG. 12).

Hypothesis of C6 oxidation or ester formation at C1 position would result in oxidation along the cellulose chain by an uncontrolled reaction of GH61 during hydrogen abstraction without subsequent cleavage. Inversely, hydrogen abstraction at C4 or C1 positions leads to the formation of copper hydroperoxo intermediate and subsequent cleavage of glycosidic bond. Multiple oxidations may result in oligosaccharides with both C1 and C4 oxidation on each side of the chain and even carboxylate group in one of the C6 end. Such modification could offer advantage of better solubility of the products.

---

The invention claimed is:

1. A composition comprising at least:
   a) An enzyme cocktail of cellulases from *Trichoderma reesei*, and
   b) One of (i) an enzyme cocktail from *Pycnoporus cinnabarinus* comprising a cellobiose dehydrogenase (CDH) or (ii) a recombinant cellobiose dehydrogenase from *Pycnoporus cinnabarinus*,
   wherein said composition does not comprise a Family 61 glycoside hydrolase.

2. The composition according to claim 1, further comprising a β-glucosidase.

3. The composition according to claim 1, further comprising a β-glucosidase from *Aspergillus niger*.

4. The composition according to claim 1, further comprising an enzyme cocktail from *Aspergillus niger* comprising a β-glucosidase.

5. The composition according to claim 1, wherein said recombinant cellobiose dehydrogenase comprises the sequence of SEQ ID NO: 1 or SEQ ID NO: 2.

6. A method for degrading a lignocellulosic biomass, comprising treating said lignocellulosic biomass with the composition according to claim 1.

7. A method for producing a fermentation product from a lignocellulosic biomass, said method comprising the following steps:
   a) liquefying a lignocellulosic biomass by using a composition according to claim 1 in order to obtain a liquefied product having a dry weight above 20%,
   b) saccharifying the liquefied product obtained from step a) with an enzyme cocktail to obtain a saccharification product,
   c) fermenting the saccharification product obtained from step b) by using a fermenting microorganism to obtain a fermentation product.

8. The method according to claim 7, wherein said fermentation product is an alcohol, an organic acid, a ketone, an amino acid, or a gas.

9. The method according to claim 7, wherein the liquefying a lignocellulosic biomass takes place for up to about 6 hours and is realized at a temperature not exceeding 90° C.

10. The method according to claim 7, wherein the dry weight of the liquefied product in step a), is of at least 25%.

11. The method according to claim 7, wherein said saccharifying step takes places for from 20 to 100 hours and carried out at a temperature in the range from about 30 to 65° C.

12. The method according to claim 7, wherein said enzyme cocktail in step b) comprises at least two carbohydrolytic enzymes capable of degrading at least one of cellulose or hemicellulose or parts thereof from lignocellulosic biomass into at least one compound selected from the group consisting of glucose, xylose, cellobiose, gluconic acid, xylonic acid and xylobionic acid.

13. The method according to claim 7, wherein said enzyme cocktail used in saccharifying is the same composition as the composition used for liquefying.

14. The method according to claim 7, wherein the liquefying step a) and the saccharifying step b) are carried out simultaneously as an enzymatic hydrolysis step.

15. The method according to claim 7, wherein the fermenting step c) is ongoing for 24-96 hours, at a temperature not exceeding 40° C.

16. The method according to claim 7, wherein the saccharifying step b) and the fermenting step c) are carried out as a simultaneous saccharifying and fermenting step after the liquefying step a).

17. The method according to claim 16, wherein the saccharifying and fermenting step takes place for 48 hours to 72 hours and is realized at a temperature not exceeding 40° C.

18. The method according to claim 7, further comprising step d) of recovering the fermentation product from step c).

19. The method according to claim 18, wherein the fermenting in step (c) and the recovering of the fermentation product in step (d) is carried out simultaneously.

20. A method for producing gluconic acid, xylonic acid and/or xylobionic acid from a lignocellulosic biomass, wherein said method comprises the following steps:
   a) liquefying of a lignocellulosic biomass by using the composition according to claim 1 in order to obtain a liquefied product having a dry weight of at least 20%, and
   b) saccharifying the liquefied product obtained from step a) with an enzyme cocktail comprising at least two carbohydrolytic enzymes capable of degrading at least one of cellulose or hemicellulose or parts thereof from lignocellulosic biomass into at least one compound selected from the group consisting of gluconic acid, xylonic acid and xylobionic acid,
   wherein step b) produces at least one compound selected from the group consisting of gluconic acid, xylonic acid and xylobionic acid.

21. The method according to claim 20, wherein the liquefying step a) and the saccharifying step b) are carried out simultaneously as an enzymatic hydrolysis step.

22. The method according to claim 20, further comprising step c) of recovering the gluconic acid, xylonic acid and/or xylobionic acid from step b).

23. The method according to claim 6, wherein said method further comprises a step of pre-treatment of the lignocellulosic biomass before the liquefying step a) by an acid treatment at a temperature between 110-250° C.

24. The method according to claim 6, wherein said lignocellulosic biomass is selected from the group consisting of herbaceous material, agricultural residues, forestry residues, municipal solid wastes, waste paper, pulp and paper mill residues, and any combination thereof.

25. The method according to claim 24, wherein said lignocellulosic biomass is selected from the group consisting of corn stover, straw, rice, wheat, oat, barley, rye, rape, bagasse, *miscanthus*, sorghum residue, grasses, coastal Bermuda grass, switch grass, bamboo, water hyacinth, hardwood, hardwood chips, hardwood pulp, softwood, softwood pulp and softwood chips.

26. A method for the degradation of a lignocellulosic biomass, comprising mixing the composition according to claim 1 with a lignocellosic biomass.

27. A method for the production of a fermentation product from a lignocellulosic biomass, comprising mixing the composition according to claim 1 with a lignocellosic biomass to obtain a product, and fermenting the product from the mixing.

28. A method for producing a fermentation product from a lignocellulosic biomass, said method comprising the following steps:
   a) liquefying a lignocellulosic biomass by using recombinant cellobiose dehydrogenase from *Pycnoporus cinnabarinus* under temperatures between 55-90° C. in order to obtain a liquefied product having a dry weight above 20%,
   b) saccharifying the liquefied product obtained from step a) with a composition comprising at least:
      an enzyme cocktail of cellulases from *Trichoderma reesei*, and
      one of (i) an enzyme cocktail from *Pycnoporus cinnabarinus* comprising a cellobiose dehydrogenase (CDH) or (ii) a recombinant cellobiose dehydrogenase from *Pycnoporus cinnabarinus*,
   wherein said composition does not comprise a Family 61 glycoside hydrolase, to obtain a saccharification product, and
   c) fermenting the saccharification product obtained from step b) by using a fermenting microorganism.

* * * * *